United States Patent
Bishop et al.

(10) Patent No.: US 6,206,878 B1
(45) Date of Patent: Mar. 27, 2001

(54) CONDITION RESPONSIVE GAS FLOW ADJUSTMENT IN GAS-ASSISTED ELECTROSURGERY

(75) Inventors: David K. Bishop; James C. Crenner, both of Littleton, CO (US)

(73) Assignee: Aspen Laboratories, Inc., Englewood, CO (US)

( * ) Notice: Subject to any disclaimer, the term of this patent is extended or adjusted under 35 U.S.C. 154(b) by 0 days.

(21) Appl. No.: 09/307,293

(22) Filed: May 7, 1999

(51) Int. Cl.[7] .................................................. A61B 18/18
(52) U.S. Cl. ........................ 606/49; 606/40; 219/121.55
(58) Field of Search ........................... 606/37–42, 45–50; 219/121.51, 121.55

(56) References Cited

U.S. PATENT DOCUMENTS

| | | |
|---|---|---|
| Re. 34,432 | 11/1993 | Bertrand . |
| Re. 34,780 | 11/1994 | Trenconsky et al. . |
| 4,040,426 | 8/1977 | Morrison, Jr. . |
| 4,057,064 | 11/1977 | Morrison, Jr. et al. . |
| 4,060,088 | 11/1977 | Morrison, Jr. et al. . |
| 4,781,175 * | 11/1988 | McGreevy et al. ............ 606/40 |
| 4,901,720 | 2/1990 | Bertrand . |
| 5,041,110 | 8/1991 | Fleenor . |
| 5,088,997 | 2/1992 | Delahuerga et al. . |
| 5,244,462 * | 9/1993 | Delahuerga et al. ............ 606/42 |
| 5,330,469 * | 7/1994 | Fleenor ............................ 606/40 |
| 5,720,745 | 2/1998 | Farin et al. . |

OTHER PUBLICATIONS

Dennis, et al., Evaluation of Electrofulguration in Control of Bleeding of Experimental Gastric Ulcers, Nov. 1979.
ERBE APC 300 Argon Plasma Coagulation Unit for Endoscopic Applications.
ERBE APC 300 Service Manual, 1997.
ConMed Corporation, Operator's Manual—System 7500 Electrosurgical Generator + ABC Modes, 1999.

* cited by examiner

Primary Examiner—Michael Peffley
(74) Attorney, Agent, or Firm—John R. Ley; L. Jon Lindsay

(57) ABSTRACT

A gas delivery apparatus used in gas-assisted electrocoagulation temporarily reduces a gas flow rate in a flowpath to an application which applies the flow of gas and electrical energy to the tissue during an arc initiation sequence. The reduced gas flow rate enhances the arc initiation capabilities and reduces the possibilities of embolism. After the arc initiation sequence is complete, the gas flow rate returns to a greater rate used during electrocoagulation. The back pressure in the flowpath and a user requested flow rate are control variables used to reduce the flow rate upon the occurrence of back pressure-related conditions and to increase the flow rate after the dissipation of those back pressure conditions.

61 Claims, 8 Drawing Sheets

CONDITION RESPONSIVE GAS FLOW ADJUSTMENT IN GAS-ASSISTED ELECTROSURGERY

This invention relates to gas-assisted electrosurgery of the type which was pioneered as a result of the invention described in U.S. Pat. No. 4,781,175. More particularly, the present invention relates to a new and improved method and apparatus for controlling the gas flow used in gas-assisted electrosurgery in relation to gas flow and back pressure conditions. A consequence of the improvements of the present invention is a reduction in the circumstances where risks of gas embolism and inappropriate operating conditions may occur.

BACKGROUND OF THE INVENTION

Gas-assisted electrosurgery is used to coagulate or stop blood flowing from the tissue at a surgical site. Gas-assisted electrocoagulation involves transferring arcs of electrical energy and ionized conductive pathways in a gas stream flowing to the tissue. The gas stream has the advantage of clearing blood from the tissue and allowing the arcs of electrical energy to directly enter the tissue and create a reticulum in the tissue. The reticulum forms a matrix-like structure in which the blood naturally coagulates, thereby sealing the tissue to further blood flow. Very substantial advantages result from this form of gas-assisted electrosurgery. Coagulation occurs more quickly. Coagulation is possible under conditions where coagulation was previously impossible or difficult to achieve. Less blood is lost during surgery, and the surgical procedure is completed more quickly. The high integrity of the sealed surface of the tissue, known as an eschar, almost eliminates the possibility of subsequent re-bleeding after the procedure is completed. Healing occurs more quickly because the eschar is thinner and more uniform compared to the eschar achieved by using standard, non-gas electrosurgical techniques.

Despite the numerous and significant advantages of gas-assisted electrocoagulation, certain concerns about its use have arisen. Perhaps the most significant concern is one relating to the risk of gas embolism in the patient. Gas embolism is the introduction of gas into the bloodstream of the patient. If the amount of gas in the bloodstream is significant and it accumulates in the heart, the heart can no longer pump blood. If used properly, gas-assisted electrocoagulation is safe because of its ability to rapidly coagulate and seal the tissue prior to the introduction of substantial amounts of gas. The skill of the surgeon in avoiding circumstances where gas embolism might occur, and the quality of the equipment used in the gas-assisted electrocoagulation, can influence the risks of gas embolism.

One very effective technique of avoiding gas embolism is to initiate the transfer of the arcs in the gas stream in a reliable manner and at a sufficiently-spaced distance from the tissue where the impact of the gas on the tissue does not force excessive amounts of gas into the tissue, but still causes the gas to clear blood and other fluid accumulated on the surface or stroma of the tissue. U.S. Pat. Nos. 4,781,175 and Re 34,432 describe techniques for assuring that the electrical arcs will initiate at such a distance.

Other types of gas-assisted electrocoagulation equipment use a standard, non-gas electrosurgical generator combined with a separate gas delivery device. These combination devices generally do not possess any additional arc initiation capability other than that available for initiating arcs in the still-air environment in which the standard electrosurgical generator is normally used. A still-air environment presents less difficulty in initiating arc transfer than in a flowing gas environment, because the flowing gas tends to disperse the ionized species and make it more difficult to initiate the arc transfer to the tissue. When a standard electrosurgical generator is combined with a separate gas delivery system, the gas flow may tend to "blow out" the arcs and the ionized species, making it very difficult or impossible to initiate the arc transfer to the tissue. To counteract this difficulty in initiating the arc transfer, the natural reaction is to bring the gas delivery nozzle of the applicator device into close proximity with the tissue. This slows the gas flow as a result of the inherent back pressure resulting from the close positioning. With a reduced gas flow, it is easier for the standard electrosurgical generator to initiate the arc transfer. Once the arcs are initiated, they are more easily sustained and the surgeon can withdraw the applicator to a working distance. However, a level of skill and recognition must be used by the surgeon to avoid the gas embolism risk associated with initiating the arc transfer at close working distances. Not all surgeons have this capability or even recognize the possibility of gas embolism from the incorrect use of gas-assisted electrosurgery.

The issue of positioning the gas nozzle of the applicator has recently become important because of the increasing use of gas-assisted electrosurgery in minimally invasive surgery, such as gastrointestinal, endoscopic and laparoscopic surgery. In minimally invasive gas-assisted electrosurgery, a relatively long tube-like applicator is inserted into the patient without making an open incision. A miniature camera or optical lens is also placed inside the patient for the surgeon to view the surgical site. Once the electrosurgical applicator is located in the appropriate position, the gas and electrical energy are delivered from the nozzle at the end of the tube-like applicator to achieve coagulation at the surgical site.

Gas-assisted electrosurgery is considered an advantage in minimally invasive surgery because of the very effective coagulation which can be achieved in a variety of difficult conditions and without necessitating the degree of control and precision in placement required to achieve good coagulation with standard, non-gas electrosurgery under similar conditions. Placement is particularly important because it is very difficult to visualize the surgical site and the position of the applicator relative to the tissue with the monoscopic view available to the surgeon through the miniature camera or optical lens. In other words, the surgeon does not have the benefit of depth perception when viewing the surgical site monoscopically, making positioning very difficult. Indeed, it is not uncommon for the surgeon to fail to realize that the nozzle of the applicator is either in contact with or buried into the tissue. Such conditions are highly conducive to a risk of gas embolism because the gas may directly enter the tissue. In conditions where the nozzle is adequately spaced from the tissue, the more uniform coagulation effects available from gas-assisted electrosurgery compensate for the lack of position recognition available to the surgeon.

It is with respect to these and other considerations, that the present invention has evolved.

SUMMARY OF THE INVENTION

One of the improvements available from the present invention involves automatically controlling the flow rate of the gas in such a manner as to achieve a more reliable arc initiation without increasing the risk of gas embolism. In accordance with this aspect of the invention, the relatively high gas flow rate selected by the surgeon for gas-assisted electrosurgery is automatically and temporarily reduced to a relatively lower flow rate for the purposes of initiating the arc transfer. Once arcing starts, the gas flow rate is automatically adjusted back to the desired higher flow rate so that normal gas-assisted electrosurgery can progress at the selected gas flow rate. The automatic reduction in gas flow rate for purposes of arc initiation assures that the arc initiation conditions will be more reliable and consistent even when used in conjunction with electrical power control techniques employed to enhance the arc initiation, such as those described in U.S. Pat. Nos. 4,781,175 and Re 34,432. This improvement is particularly significant in those types of gas-assisted electrocoagulation where a standard, non-gas electrosurgical generator is combined with a separate gas delivery apparatus. The improvement of initially reducing the gas flow rate allows the standard electrosurgical generator to more reliably initiate the arc transfer, because the lower gas flow rate is more conducive to initiating the arc transfer. Furthermore, the lower gas flow rate during initiation reduces the risk of embolism compared to the circumstance where the higher gas flow rate impacts the tissue at a close distance.

The improvement of reducing the gas flow during arc initiation is particularly beneficial in minimally invasive surgery. Should the nozzle be positioned close to the tissue or buried in the tissue, the reduced gas flow during arc initiation reduces the risk of gas embolism because a lesser quantity of gas is initially delivered. The reduced flow rate during arc initiation allows a check of whether an occlusion is in place at a reduced risk rate of gas flow. Should an occlusion be in place, the flow at the lower rate will be maintained or an alarm will be set which also inhibits the gas flow.

The improvement of reducing the gas flow during arc initiation is also important in those gas-assisted electrocoagulation systems which combine a standard, non-gas electrosurgical generator with a separate gas delivery apparatus. Most of these types of combined systems did not previously have any capability of enhancing the arc initiating capability, because the standard, non-gas electrosurgical generator had no provisions for adjusting the power output to accommodate arc initiation. The improvements of the present invention can be incorporated in the gas delivery apparatus so that when it is used in combination with a standard, non-gas electrosurgical generator, the combined system will have an enhanced ability to initiate arc transfer to the tissue at a reduced risk of gas embolism.

Another one of the improvements available from the present invention relates to a capability of automatically reducing the gas flow rate under circumstances where a partial occlusion occurs. Generally, a partial occlusion will result from the nozzle of the applicator being too close to or embedded in the tissue. Such partial occlusions can occur before or after the arc transfer has been initiated during the course of the procedure, as a result of the surgeon moving the nozzle into or too close to the tissue. Such circumstances can also create a risk of gas embolism. In accordance with this aspect of the invention, the back pressure in the gas delivery tube is sensed and when it exceeds a predetermined value, the normal operating gas flow rate is reduced in increments until the reduction in gas flow rate results in an acceptable level of back pressure which is not likely to increase the risks of gas embolism. Should the occlusion dissipate and the back pressure decrease as a result, the gas flow rate will be automatically adjusted upwardly in increments until the user requested operating gas flow rate has been achieved or until that maximum amount of gas flow consistent with an acceptable back pressure has been achieved. This improvement of continually evaluating the back pressure and adjusting the gas flow, both upwardly and downwardly, further serves to reduce the risks of gas embolism while maintaining the possibility of returning to the desired operating conditions selected by the surgeon.

Another one of the improvements available from the present invention relates to sensing the back pressure associated with a particular type of applicator, and adjusting the gas flow rate to an acceptable value for that type of applicator. Adjusting the gas flow rate to a proper operating range for different types and categories of applicators results in a greater assurance that the flow conditions for that type of applicator are the most conducive to promote arc initiation to the tissue and to reduce risks of gas embolism, both during arc initiation and during continued use of the applicator.

A further improvement available from the present invention relates to sensing the back pressure under all operating conditions and disabling the transfer of gas and electrical energy to the tissue when serious risk conditions occur. By disabling the transfer of gas and electrical energy to the tissue, the surgeon is forced to take corrective action.

A more complete appreciation of the present invention and its scope, and the manner in which it achieves the above noted improvements, can be obtained by reference to the following detailed description of presently preferred embodiments of the invention taken in connection with the accompanying drawings, which are briefly summarized below, and the appended claims.

DETAILED DESCRIPTION

Figure 1:
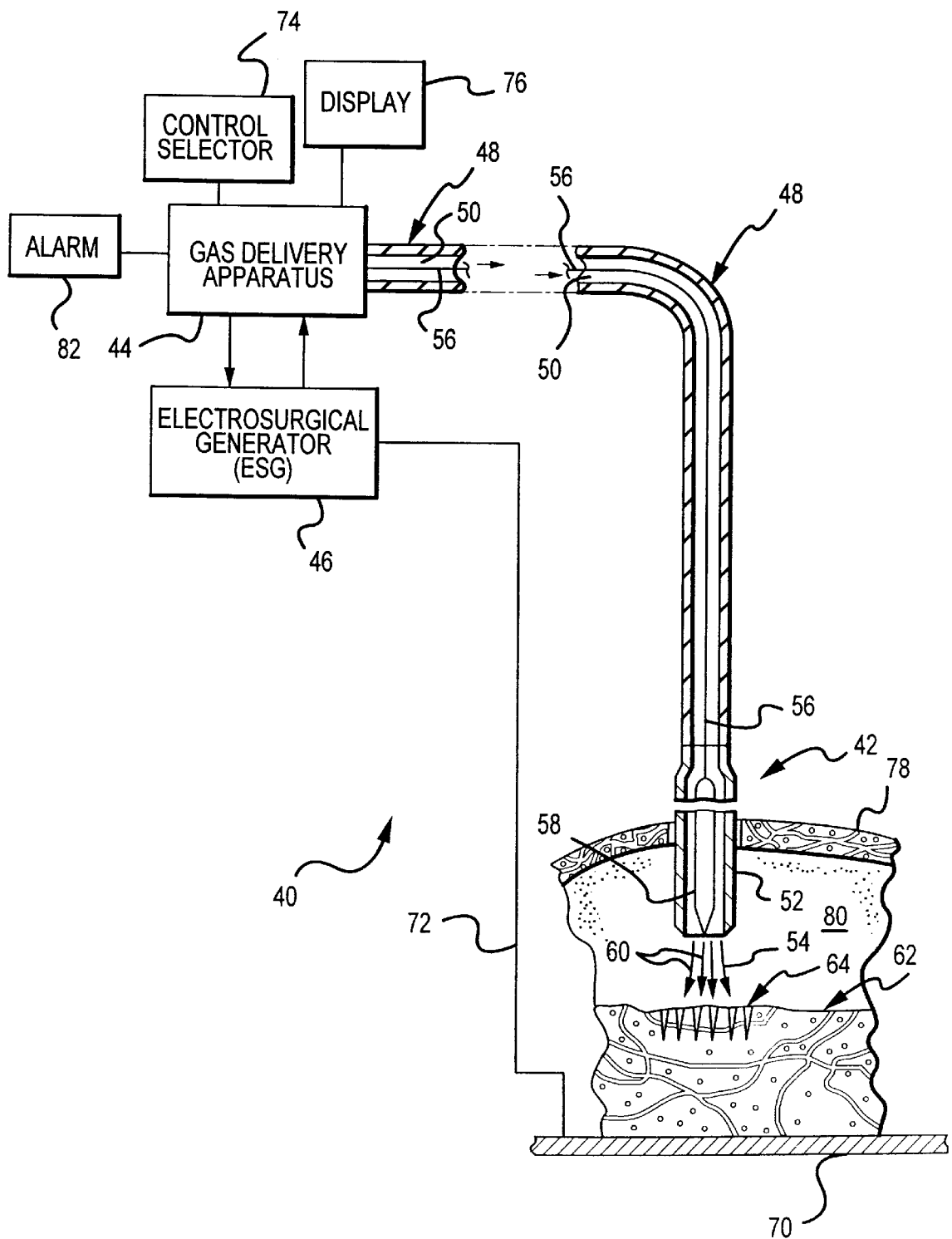
FIG. 1 is a generalized illustration of a gas-assisted electrosurgical unit embodying the present invention, illustrating a gas delivery apparatus, an electrosurgical generator and then applicator employed in an exemplary surgical procedure on tissue.

A gas-assisted electrosurgical unit (ESU) which embodies the present invention is illustrated generally in FIG. 1 and is referenced 40. The ESU 40 includes three major components: an applicator 42, such as a pencil-type handpiece used in open surgery or a tube-like probe used in minimally invasive surgery; a gas delivery apparatus 44; and an electrosurgical generator (ESG) 46. The gas delivery apparatus 44 and the ESG 46 may be combined into a single unit as described in U.S. Pat. No. 4,781,175, or each of them (44 and 46) may be separate but operatively interconnected as described in U.S. Pat. Nos. 5,041,110 and 5,330,469. A flexible cord 48 connects the gas delivery apparatus 44 to the applicator 42. The ESG 46 is connected to deliver radio frequency (RF) electrical energy to the gas delivery apparatus 44, and the electrical energy from the ESG 44 is conducted through the gas delivery apparatus 44 to a cord 48. In the case of the applicator 42 being a minimally invasive surgical probe, the flexible cord 48 may be an extension of a tube-like portion of the probe itself.

The gas delivery apparatus 44 delivers a predetermined flow of gas through a conduit 50 within the cord 48 to the applicator 42. The gas issues from a nozzle 52 located in at the distal end of the applicator 42 in a directed or substantially laminar flow stream or jet 54. The electrical energy supplied by the ESG 46 is conducted through the gas delivery apparatus 44 and is conducted by a conductor 56 located within the conduit 50 of the cord 48. The conductor 56 is electrically connected to a needle-like electrode 58 which is located in the nozzle 52. The electrical energy supplied by the ESG 46 ionizes the gas flowing around the electrode 58 and through the nozzle 52 to create ionized conductive pathways in the jet 54. The gas delivery apparatus 44, the cord 48 and the nozzle 52 are one example of means for conducting a predetermined gas in a jet 54. The ESG 46, the cord 48 and the electrode 58 are one example of means for transferring electrical energy in ionized conductive pathways in the gas jet 54.

In an active mode of operation of the ESU 40, electrical energy is transferred in the ionized conductive pathways in the jet 54 in the form of arcs 60. The arcs 60 travel within the jet 54 until they reach tissue 62 of the patient at the electrosurgical site. The gas flow from the jet 54 pushes accumulated blood from the surface or stroma of the tissue 62 and allows the electrical arcs 60 to enter the tissue 62 without being diverted into the conductive blood. The electrical arcs 60 create a reticulum 64 of arc-created holes in the tissue 62. The natural coagulating mechanism of blood is activated by the reticulum 64, which results in blood coagulation, stoppage of further bleeding, and sealing of the tissue. The sealing coagulated layer at the surface or stroma of the tissue forms what is known as an "eschar." Details of the characteristics of the type of eschar created from gas-assisted electrosurgery, and the significant advantages of gas-assisted electrosurgery, are more particularly described in U.S. Pat. No. 4,781,175.

The electrical energy of the arcs 60 travels through the gas jet 54, to the tissue 62, and through the tissue 62 to a return electrode or patient plate 70 which contacts the tissue 62 of the patient. The patient plate 70 is connected by a return electrical conductor 72 to the ESG 46. A complete electrical circuit is thus established for conducting current from the ESG 46, to the electrode 58 in the nozzle 52, through the jet 54, to and through the tissue 62, to the patient plate 70, through the return conductor 72 and back to the ESG 46. This type of circuit connection where the electrical energy flows from the applicator through the patient tissue to a return electrode which is located remotely from the surgical site is typically referred to as "monopolar" electrosurgery.

When the surgeon activates or "keys" the ESU 40 for the delivery of electrosurgical power to the tissue 62, the ionized conductive pathways within the gas jet 54 are first established. The ionized state of ionized conductive pathways in the gas jet 54 create a corona or glow discharge within the jet 54, and the glow discharge or corona is capable of initiating arc conduction when the surgeon moves the nozzle 52 into operative proximity with the tissue 62. When the nozzle 52 is positioned in operative proximity with the tissue 62, the ionized conductive pathways to the tissue 62 establish enough of a closed circuit through the tissue 62 to commence or initiate the arc transfer in the jet 54 to the tissue 62. Without maintaining the gas in a sufficiently ionized state to create enough ionized species in the gas jet 54, it is impossible or extremely difficult to repeatedly and reliably initiate the transfer of arcs 60 in the gas jet 54 to the tissue 62. A relatively high flow rate of gas through the nozzle 52 makes it difficult to sustain the ionized conductive pathways in the gas jet to reliably and consistently initiate the transfer of arcs 60 to the tissue 62, particularly with an ESG 46 having a low power output and a diminished capability to transfer significant power into relatively high load impedances.

The ESG 46 includes conventional dials and control selectors 74 for the surgeon to select the amount of and conditions for electrical energy to be delivered. The conventional dials and control selectors 74 are also included when the ESG 46 and the gas delivery apparatus 44 are enclosed in a single unit. Similarly, dials and control selectors 74 are a part of the gas delivery apparatus 44 which allows the surgeon to select the amount of gas flow to be delivered to the surgical site. A display 76 displays the quantity of gas flow as well as other information. The flow rate displayed at 76 may change during the use of the ESU 40 to reflect the different flow conditions from the nozzle 52. The control selector 74 is also intended to represent the conventional switches (foot and finger) which the surgeon depresses to activate the ESU 40. Releasing the activation switches deactivates the ESU 40, terminating the flow of gas and electrical energy.

Gas-assisted electrosurgery may be conducted in open surgical conditions where an open incision is made and the tissue is exposed to the open atmosphere. Under such circumstances, the surgeon typically holds a pencil-like applicator 42 and moves it relative to the tissue to accomplish the coagulation. In most cases, the open procedure does not make it difficult to visualize the surgical site or the relative position of the nozzle 52 from the tissue. However, in aggressive bleeding situations the surgeon may insert the nozzle 52 into the rapidly accumulating blood and not be able to gauge the distance of the nozzle from the tissue. Under circumstances where the patient has an atypical physiology or an unusual placement of the incision arises, the surgeon may be required to position the nozzle relative to tissue in a manner which cannot be seen, making it difficult to gauge the relative placement of the nozzle from the tissue. Under these circumstances, the nozzle may be placed against the tissue and the tissue may partially occlude the nozzle, increasing the risk of gas embolism.

Visualizing the surgical site is more difficult under minimally invasive surgical conditions, where a direct stereoscopic view is not possible. FIG. 1 illustrates the minimally invasive surgical condition by illustrating the nozzle 52 of the applicator 42 inserted through an abdominal wall 78. Although not all of the details of this conventional laparoscopic surgical situation are shown, the abdominal wall 78 is held away from the tissue 62 by insufflation gas pressure supplied into the abdominal cavity 80. A miniature camera (not shown) is also inserted within the abdominal cavity 80 by which the surgeon views the surgical site. The insufflation gas pressure also forms an impediment or resistance which must be overcome by the gas flow which is delivered from the nozzle 52. Thus in laparoscopic situations, the insufflating gas pressure restricts or alters the flow rate characteristics of the gas jet 54, particularly when pressure regulators rather than mass flow regulators control the gas flow. A mass flow regulator will deliver gas flow rates based on mass flow which is less influenced by back pressure. Consequently, a mass flow regulator gas delivery apparatus 44 is more likely to continue to deliver gas flow in partially occluded situations or in situations where the nozzle 52 is closely positioned relative to the tissue 62. Pressure regulator systems tend to diminish the amount of gas flow delivered under back pressure conditions, but pressure regulator systems are not as accurate or reliable in other circumstances.

An endoscopic surgical situation is also represented by FIG. 1, in the sense that the applicator 42 and the nozzle 52 are inserted inside the body of the patient. In endoscopic applications, usually an optical lens system (not shown) is part of the probe applicator 42. FIG. 1 also represents a gastrointestinal surgical situation, except that the probe applicator 42 is usually inserted into a normal body passageway such as the esophagus and the stomach. Endoscopic and gastrointestinal surgical sites are not normally pressurized with an insuflating gas.

The present invention focuses on an automatic capability of the gas delivery apparatus 44 to adjust the gas flow rate under various operative electrosurgical conditions and in response to the type of applicator 42 attached to the gas delivery apparatus 44. The condition-responsive gas flow adjustment characteristics of the present invention are particularly useful in minimizing the risks of gas embolism, despite the skill level of the surgeon. The flow adjustment characteristics of the present invention are also useful in establishing the best operative conditions for different types of applicators 42. The gas delivery apparatus 40 of the present invention will also terminate the transfer of gas and electrical energy under gas flow conditions which are inappropriate for the continuance of the procedure. Under these conditions the gas delivery apparatus 44 energizes an alarm 82 to notify the surgeon of these conditions. The gas-flow adjustment characteristics of the gas delivery apparatus are applicable for use with an ESG 46 specifically used for gas-assisted electrocoagulation or for use with an ESG 46 of the type which is primarily intended for standard, non-gas electrosurgery. When used with a standard, non-gas ESG 46, an improved ability to control electrosurgical conditions that might give rise to gas embolism risks is achieved.

Details of the gas delivery apparatus 44 are described with reference to FIG. 2. The gas delivery apparatus 44 produces a regulated gas mass flow rate from a gas flowpath 98 which is supplied to the conduit 50 of the cord 48 and conducted to the nozzle 52 (FIG. 1). The mass flow regulation is accomplish by use of a closed loop control system, where the user requested mass flow rate is compared with the measured mass flow rate, an error signal is developed with regard to the difference, and the gas flow in a gas flowpath 98 is adjusted until the control loop is stabilized.

The gas delivery apparatus 44 includes a gas source 100, a pressure regulator 102, a pneumatic manifold 104, a sensing orifice 106, and a filter 108. The gas source 100 may be a conventional tank of argon gas pressurized initially to about 3000 psi, to provide the gas to the pressure regulator 102. The present invention supplies argon gas, or any other inert gasses that can be ionized with RF energy for clinical applications in electrosurgery. A pressure gauge 110 is preferably interposed between the argon gas source 100 and the pressure regulator 102 to indicate the amount of gas remaining in the gas tank. The pressure regulator 102 reduces the pressure from the gas source 100 to a low pressure, preferably about 20 to 30 psi, and provides this low pressure gas to the pneumatic manifold 104. The secondary or output side of the pressure regulator 102 preferably has a pressure relief valve 112 connected to it as a fail-safe mechanism. The pressure relief valve 112 opens at about 50 psi in the event that the pressure regulator 102 fails to reduce the pressure at its output.

The pneumatic manifold 104 includes electrically-controlled valves 114 and 116 for controlling and regulating the mass flow rate of gas in the flowpath 98. Preferably, the pneumatic manifold 104 includes a solenoid valve 114, which opens whenever the ESU 40 (FIG. 1) is activated for use and closes whenever the ESU 40 is de-activated. A proportioning valve 116 regulates the gas mass flow rate delivered in the flowpath 98. The proportioning valve 116 increases and decreases gas flow as a result of a control signal (156) applied to it. Optionally, a flow damper (not shown) may be placed downstream from the proportioning valve 116 to dampen any minor fluctuations or oscillations of the gas flow that may occur as a result of the flow variations from the proportioning valve 116.

The sensing orifice 106 includes a calibrated flow restriction 118 that reduces the pressure from an inlet 120 of the sensing orifice 106 to an outlet 122 of the sensing orifice 106. The differential pressure across the sensing orifice 106 is the basis for the gas flow rate control information used in the mass flow control loop. The differential pressure across the sensing orifice 106 between the inlet 120 and the outlet 122 is proportional to the gas flow rate in the flowpath 98. An increase in flow rate causes an increase in differential pressure, and a decrease in flow rate causes a decrease in differential pressure measured across the calibrated restriction 118. Hoses 124 and 126 connect to the inlet 120 and the outlet 122 on opposite sides of the calibrated restriction 118 to provide the differential pressure information to a differential pressure transducer 132. A third hose 128 is connected at a location downstream of the calibrated restriction 118 to an absolute pressure transducer 134. The absolute pressure transducer 134 initially provides pressure information relative to atmospheric pressure in the flowpath 98 downstream of the sensing orifice 106. Initially, before gas flows through the flowpath 98, the ambient atmospheric air pressure corresponding to the sea level altitude where the ESU 40 is in use is sensed by the transducer 134 through the third hose 128. The atmospheric pressure information is used to compensate the quantity of gas delivered according to different altitudes. The altitude-related signal is referred to below as the reference (or Ref) signal. When gas flows in the flowpath 98, the absolute pressure transducer 134 measures the gas back pressure in the flowpath 98.

The filter 108 is included in the gas flowpath 98 downstream of the sensing orifice 106 to ensure the delivery of clean argon gas into the cord 48, to the nozzle 52, and to the tissue 62 (FIG. 1). A connector (not shown) couples the gas in the gas flowpath 98 into the end of the cord 48. Electrical energy from the ESG 46 is also preferably coupled through this same connector (not shown) to the conductor 56 located in the conduit 50 of the cord 48 (FIG. 1).

The differential pressure transducer 132 supplies an output voltage signal on line 130 that is proportional to the differential pressure across the flow restriction 118 at the sensing orifice 106. The voltage signal at 130 from the differential pressure transducer 132 is provided to an amplifier 138 which amplifies the voltage signal at 130 to provide an output voltage signal called dP (delta pressure) on line 140. The dP signal at 140 is proportional to the flow rate of gas through the sensing orifice 106.

The absolute pressure transducer 134 supplies an output voltage signal on the line 136 that is proportional to the absolute pressure sensed downstream of the calibrated restriction 118. The signal at 136 is proportional to the back pressure caused by the applicator, caused by the position of the applicator relative to the tissue or caused by an occlusion, while gas flows in the flowpath 98. The voltage signal at 136 from the absolute pressure transducer 134 is provided to an amplifier 142 which amplifies the voltage signal and provides an output voltage called $P_{ABS}$ (absolute pressure) on line 144. The $P_{ABS}$ signal on line 144 is proportional to the absolute pressure sensed by the transducer 134.

The output voltage signals dP and $P_{ABS}$ on lines 140 and 144, respectively, are supplied to an analog multiplier 146 that multiplies the two signals 140 and 144. The resulting product output signal at 148 from the multiplier 146 is linearly proportional to the measured mass flow rate of the gas conducted through the flowpath 98. The relationship of the delta pressure represented by signal 140 and the absolute pressure represented by the signal 144 to measured flow rate represented by signal 148 is well known. The output signal at 148 therefore represents the measured mass flow rate of gas flowing through the flowpath 98.

The $P_{ABS}$ voltage signal is also supplied as an input signal to an amplifier 147. An output signal from the amplifier 147 is supplied at 149 as a voltage signal (PMEA) related to the measured back pressure of the gas flow through the flowpath 98, or the ambient atmospheric pressure when no gas is flowing through the flowpath 98. The PMEA signal at 149 is applied as one input signal to a control loop microcontroller 150. An analog-to-digital converter (not shown, but included with the microcontroller 150) converts the PMEA voltage signal into a digital signal for use by the microcontroller 150.

The microcontroller 150 is connected to the flow control selector 74 to receive various user request input signals including activation requests from the surgeon. The signal at 153 is related to the user request gas flow rate selected by the surgeon.

The microcontroller 150 establishes a display flow rate output signal (VGAS) at 151 which initially is established by the user request input signal at 153. The signal VGAS at 151 is referred to as the displayed flow rate, and this signal is presented to the user at the display 76. In cases of safe and normal operation, the displayed flow rate signal (VGAS) will essentially correspond to the value represented by the user request signal at 153. However, under some circumstances as discussed below, the displayed flow rate signal VGAS at 151 may be modified by action of the microcontroller 150 in response to the value of the measured back pressure signal PMEA at 149. Under such circumstances, the VGAS quantity presented at the display 76 will differ from the quantity represented by the user request signal 153. The VGAS signal is an analog signal created by a digital-to-analog (D/A) converter (not shown) included with the microcontroller 150.

The measured mass flow rate voltage signal at 148 from the analog multiplier 146 is amplified by an amplifier 152 and the resulting signal at 155 is compared to the VGAS signal at 151 by a differential amplifier 154. Thus, the displayed flow rate represented by the VGAS signal is compared to the measured mass gas flow rate signal at 155. Any difference between the measured mass gas flow rate signal and the displayed flow rate signal is represented by a control signal at 156 supplied by the differential amplifier 154. The control signal at 156 will cause an adjustment to the flow established by the proportioning valve 116, thereby increasing or decreasing the flow rate of gas through the proportioning valve 116. When the measured flow rate (signal 155) exceeds the displayed flow rate (signal 151), the control signal 156 delivered to the proportioning valve 116 will reduce the gas flow. Conversely, when the measured flow rate is less than the displayed flow rate, the control signal 156 causes the proportioning valve 116 to increase the gas flow through the flowpath 98. As the measured mass gas flow rate changes with different flow conditions at the operating site, the described control loop will alter the control signal at 156 until a steady state gas flow rate which corresponds to the user requested or allowed gas flow rate is obtained. A conventional emitter follower circuit (not shown) receives the control signal 156 and drives current to the proportioning valve 116 in relation to the value of the control signal 156.

When the measured back pressure (PMEA) exceeds defined limit conditions, corrective and operation-inhibiting actions are taken, according to the operational mode of the ESU and its gas flow setting. The back pressure signal PMEA 149 is monitored by the microcontroller to obtain these functions. If the back pressure exceeds a predetermined limit, the operation of the gas delivery apparatus 44 shuts off, and the solenoid valve 114 and proportioning valve 116 are closed to terminate the delivery of gas. When a hazardous occlusion condition occurs, it is preferable to terminate the gas flow through the gas flowpath 98 and terminate the delivery of the RF electrical energy from the ESG 46 (FIG. 1), provide an audible warning (such as a beep or tone) to the surgeon from the alarm 82 (FIG. 1), and provide a visual indication (such as an error code or message) on the display 76 of the condition that caused the shut down. Less hazardous partial occlusions, transitory minor occlusions and certain other control conditions cause a reduction in the gas flow delivered in the flowpath 98.

Since the gas flow rate is controlled by mass flow closed loop regulation, the gas flow will try to be maintained even when an occlusion is blocking the gas flow from the nozzle 52. Under such circumstances, without the gas flow adjustment features described herein, an embolism or other hazardous condition could be presented. Thus, the back pressure itself within the gas flowpath 98 is used to anticipate an occlusion or other restriction in the gas flow lines and to control the gas mass flow rate when the back pressure exceeds predetermined limits. The predetermined back pressure limits are specific to different operational modes of the gas delivery apparatus and relate to the various user requested gas flow rate settings, all of which are selected by the surgeon.

When the gas delivery apparatus 44 is first turned on, the PMEA voltage signal at 149 is read and stored in the memory of the microcontroller 150. This initial value is used as a Reference (Ref) voltage or signal for the duration of the procedure, and for other purposes associated with the operational mode of the ESU, as described below. In addition, for each setting or flow rate within an allowed operational range of gas flow rates from the ESU, the PMEA voltage is anticipated to be a specific incremental value above the established reference voltage. The anticipated incremental value of the PMEA signal at each flow rate is determined empirically, and is related to the characteristics of the components used in the gas delivery apparatus 44. The anticipated incremental values for each flow rate is stored in a memory associated with the microcontroller 150, for use during the operations described below.

One of the improvements available from the present invention relates to facilitating a more reliable initiation of arc transfer energy in the gas jet 54 to the tissue, even under conditions where the ESG 46 does not have the capability to specifically modify power delivery for enhanced arc initiation. This improvement is particularly useful to avoid the gas embolism risk in those circumstances where it is necessary to bring the nozzle 52 (FIG. 1) into close proximity with the tissue to initiate the arc transfer. Under such circumstances, the close proximity of the nozzle to the tissue with the relatively high gas flow rate selected for continuous electrocoagulation might increase the risks of gas symbolism.

In general terms, the gas flow rate is temporarily reduced for purposes of enhancing arc initiation after the ESU is activated and to allow any occlusion to be detected under the less hazardous conditions of reduced gas flow. After the arc transfer has been initiated and no occlusion is sensed, the relatively higher user requested gas flow rate is then automatically delivered. This particular functionality is described in reference to FIG. 3 and is referred to herein and as "soft start."

Figure 2:
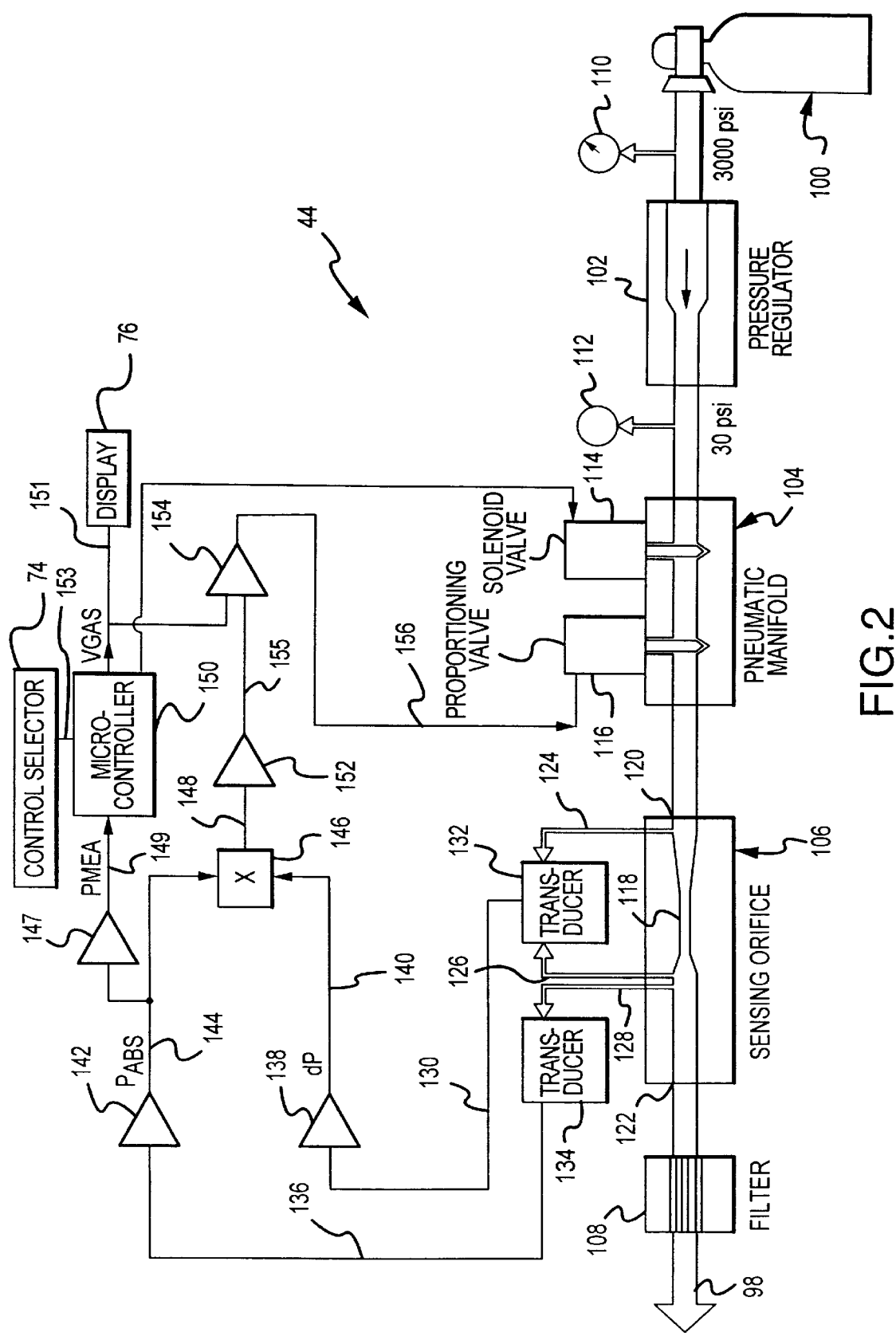
FIG. 2 is a block diagram of aspects of the gas delivery apparatus shown in FIG. 1.
Figure 3:
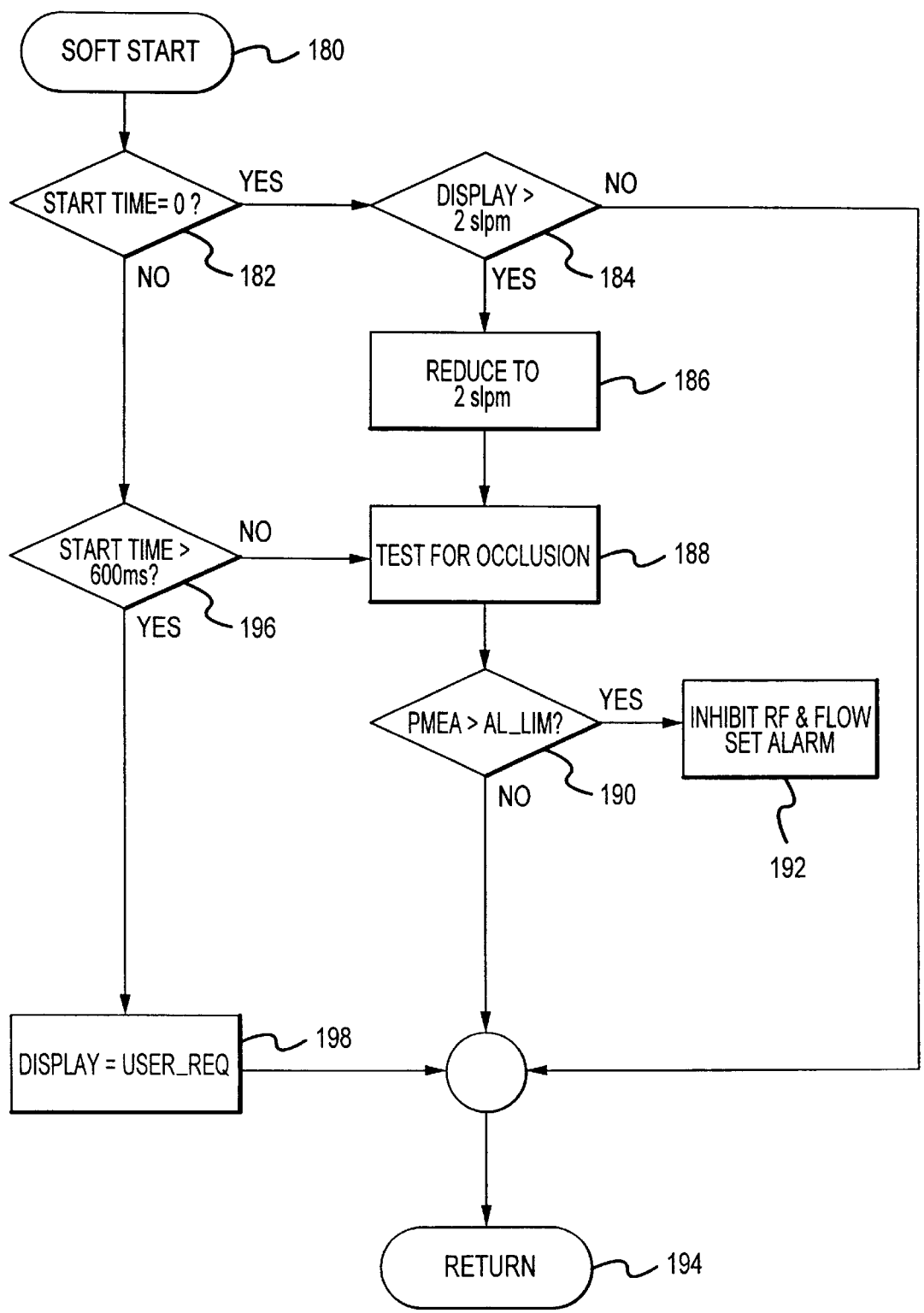
FIG. 3 is a flow chart of functions performed by the gas delivery apparatus shown in FIG. 2 during starting conditions when arcs are initially transferred to the tissue, in accordance with the present invention.

The "soft start" procedure shown in FIG. 3 is executed by the instructional code contained within the microcontroller 150 (FIG. 2). The soft start operational flow starts at step 180 and is applied during an initial period of time starting with activation of the ESU. The microcontroller 150 receives a signal indicative of the activation request from the surgeon as one of the signals from the control selector 74 (FIG. 2). In response to the activation request, a start time clock is initially started (not shown). Immediately thereafter, a determination is made at step 182 as to whether or not this is the beginning, i.e. zero time, of the soft start procedure. If so, a determination is made at step 184 of whether the display flow (which is initially the same as the user requested flow) is greater than 2 standard liters per minute (slpm). If so, the displayed gas flow rate is reduced to 2 slpm, as shown at step 188.

A test for an occlusion in the flowpath is thereafter initiated at step 188. The back pressure signal PMEA (149, FIG. 2) is tested at step 190 to determine whether it exceeds an a predetermined alarm limit (AL_LIM). The predetermined alarm limit AL_LIM referred to in FIG. 3 represents an empirically defined maximum back pressure limit which can be accepted for a flow rate of 2 slpm which is established at step 186. If the back pressure exceeds this predetermined alarm limit, and an unacceptable back pressure condition exists an alarm condition is initiated as shown at step 192. In conjunction with the alarm condition initiated at step 192, electrical energy (RF) from the ESG 46 (FIG. 1) and the gas flow rate from the gas delivery apparatus 44 (FIGS. 1 and 2) are terminated as shown at step 192, thereby de-activating the ESU. Once the ESU is de-activated at step 192, it is necessary to again initiate another activation request for continued use of the ESU, after the cause of the occlusion has been determined and corrected.

If the determination at step 190 is no, indicating that the measured back pressure (PMEA) is less than the predetermined alarm limit (AL_LIM), the procedure flow advances to step 194, and then returns from step 190 to the procedure commencement step 180. Furthermore, if the determination that the display flow rate is less than 2 slpm at step 184, the flow is sufficiently low to initiate good arc transfer to the tissue, so the program flow advances to step 194. One loop or execution of the soft start procedure flow occurs each 100 milliseconds.

With the second and subsequent loops through the soft start procedure flow, the activation time clock (not shown) has advanced to the point where the determination made at step 182 causes the program flow to advance to the determination at step 196. At step 196 the determination is made whether the time clock has exceeded 600 milliseconds, which occurs on approximately the sixth loop through the procedure shown in FIG. 3. If the determination at step 196 is no, a test for an occlusion begins at step 188, followed by execution of the subsequent functionality represented by steps 190 and 192. If the determination at step 196 is yes, the displayed flow rate is set to the user requested flow rate, as shown at step 198. Thereafter, the program flow advances to step 194.

With each subsequent pass beyond the first pass through the soft start control procedure shown in FIG. 3, and provided that no back pressure alarm and shut down condition exists, and until the elapsed time of this soft start procedure exceeds 600 seconds, the program flow advances from step 196 to steps 188, 190 and 194, thus returning for another execution of the soft start procedure at 100 msec intervals. When transitions through a sufficient number of loops of the program flow shown in FIG. 3 have occurred and the determination at step 196 is yes, the gas flow rate is then set at step 198 to present at the display 76 (FIGS. 1 and 2) the user requested gas flow rate. Thus, with the execution of step 198, the temporarily reduced gas flow rate set during the soft start procedure is thereafter set to the gas flow rate which was requested by the user, unless other control factors described below thereafter intervene.

The initially lower gas flow rate set at step 186 promotes starting the arc transfer. The arc transfer immediately starts to create an eschar which seals the tissue against the entry of gas, and the sealing effect is continued when the relatively higher gas flow rate is delivered. The amount of time during which the reduced starting gas flow rate is delivered is limited, thereby only momentarily and almost imperceptibly limiting the electrocoagulation effect from that full effect desired by the surgeon. Even if the low starting gas flow rate does not momentarily clear blood from the tissue, the very quickly occurring higher gas flow will do so. If for some reason the arc initiation has not started at the end of the soft start sequence, the delivery of the full flow rate will be recognized by the surgeon as representing a problem, at which time the surgeon should de-activate the ESU and start with another activation sequence after corrective measures have been taken.

The soft start improvement is of particular use and benefit in those combination gas-assisted ESU's using a standard, non-gas electrosurgical generator in combination with a gas delivery apparatus. The improved starting capability available from controlling the gas flow rate is comparable to that improved utility which was previously available only by modifying the electrical and power output characteristics of the ESG for starting the arc transfer. Since a typical standard, non-gas electrosurgical generator did not offer the capability to modify its electrical output characteristics for arc initiation with gas-assisted electrosurgery, most if not all such combination gas-assisted ESUs did not possess improved arc initiation characteristics. This improvement of the present invention provides such improved arc initiation characteristics without modifying the output characteristics of the ESG.

This initial low flow rate is established during the soft start procedure (step 186, FIG. 3) and is sufficient to determine whether an occlusion exists initially and to permit any occlusion to be cleared prior to flowing gas at the actual requested flow rate. It is possible for a gas embolism condition to occur almost as soon as the gas delivery apparatus is activated, and the soft start procedure will allow for the detection of such conditions. The PMEA voltage (149, FIG. 2) is sampled for an occlusion during this time period. Two effects may cause sensing and response delays before the gas flow can be terminated in response to an occlusion. The first delay effect is the amount of time required to build back pressure in the gas flowpath 98 (FIG. 2). The first delay may depend on the type of attached applicator and the requested flow rate. The second delay may be intentionally selected to anticipate some minimum but safe period of time for the occlusion to exist before responsive action is taken. This second delay allows slight intermittent or transitory restrictions on the flow to be ignored.

The chosen time period for the soft start may not be enough to detect an occlusion in all cases; however, the soft start may still provide advantages that can minimize embolism risks caused by delivery of relatively high flows of gas to the patient. The low flow rate pre-pressurizes the gas flow pathway before a higher gas flow rate starts, thereby reducing the amount of time that the higher gas flow rate will be provided before an occlusion can be detected at the higher gas flow rate. In this manner, the inadvertent flow will be delivered at the lower starting flow rate for part of the time, and the ESU 40 can be shut down afterwards before too much gas flows. Pre-pressurizing also provides pressure to the transducers 132 and 134 (FIG. 2) so that the higher requested gas flow can be regulated and stabilized with minimal or no overshoot when the soft start time period ends.

Figure 6:
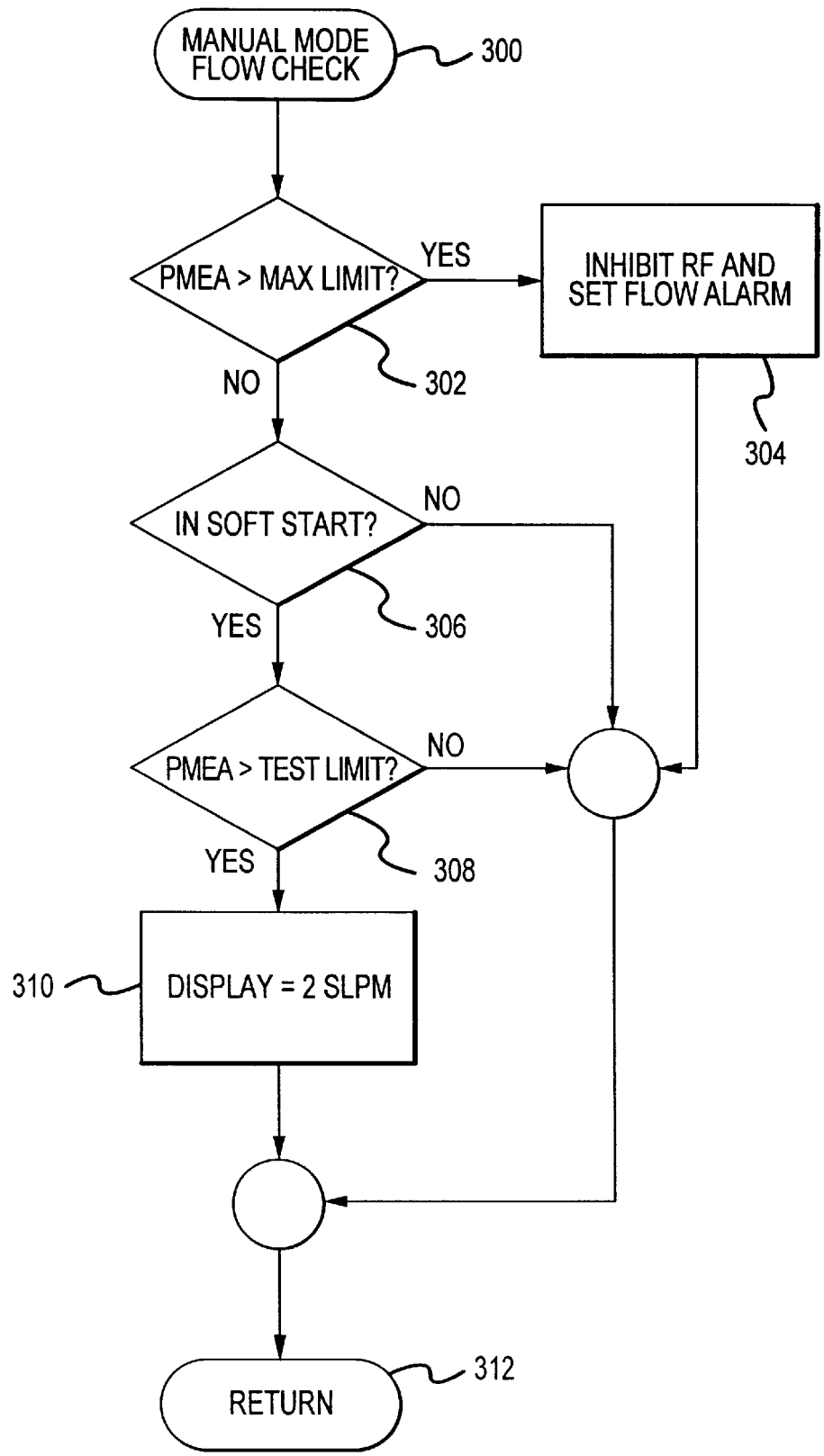
FIG. 6 is a flow chart of the functions performed by the gas delivery apparatus shown in FIG. 2 during a manual mode operating condition, in accordance with present invention.

The soft start procedure is preferably incorporated into all of the operational mode flow check procedures described below. Since the soft start procedure should occur before the below-described gas flow adjustment procedures, it is preferable to place the soft start procedure at the beginning of the flow check procedures discussed below. The manual operational mode flow check procedure described below in conjunction with FIG. 6 is so short, however, that it may also be acceptable to place the soft start procedure after the flow check procedure shown in FIG. 6.

One of the improvements of the present invention involves sensing the back pressure to determine the type of applicator connected to the gas delivery apparatus. This improvement is particularly of benefit in determining when minimally invasive applicators (endoscopic or gastrointestinal) are attached. The functionality of this particular aspect of the invention is referred to below as the "endo" mode of operation and is described more completely in FIGS. 4A, 4B and 4C. The endo mode limits the maximum allowable flow rate to 4 standard liters per minute (slpm). The flow range for the endo mode is, 0.1 to 4 slpm and is established by user-selected minimum and maximum flow limits based upon user-selected power settings.

Gastrointestinal (GI) electrosurgical probes are examples of the types of applicators used in the endo mode and are characterized by an outer diameter which ranges from about 1.5 mm to about 3.4 mm. The inner diameter may be 25% to 35% smaller. These applicators can produce a back pressure in excess of 1 pound per square inch (psi) even at very low flow rates and can even produce as much as 6 psi back pressure at 4 slpm, thus imitating the behavior of an occlusion. Such high back pressures cause the flow velocity at the orifice of the nozzle 52 (FIG. 1) to increase, which can cause arc initiation failures or short arc transfer and working distances.

When operating in the endo mode, the control microcontroller 150 will establish a maximum limit for the PMEA signal (149, FIG. 2) and, when this limit is exceeded, the flow rate will be reduced to no more than 2 slpm. The control microcontroller 150 reduces the flow rate by varying the control signal 156 (FIG. 2). By reducing the flow rate, the back pressure will be reduced and the gas velocity at the orifice of the nozzle 52 will be reduced allowing easier ionization and arc transfer. Listed below in Table 1 are exemplary limits established for flow reduction and occlusion alarm actions.

TABLE 1

| ACTION | PMEA (SLPM) | PMEA V | COMMENTS |
| --- | --- | --- | --- |
| OCCLUSION ALARM | <1.0 | Ref + 0.5 V | RF & Flow inhibited |
| OCCLUSION ALARM | >1.0 and <1.5 | Ref + 1.2 V | RF & Flow inhibited |
| OCCLUSION ALARM | >1.5 | Ref + 1.3 V | RF & Flow inhibited |
| Reduce Flow by 0.5 | >1.0 and <1.5 | Ref + 0.6 V | Reduced flow |
| Reduce Flow by 0.5 | >1.5 | Ref + 0.7 V | Reduced flow |
| Reduce by 0.5 but no lower than 0.1 | <1.0 | Ref + 0.3 V | Reduced flow |

When the PMEA signal is greater than the established reference voltage (Ref) plus an appropriate GI reference margin, such as about 0.3 V (an empirically derived value depending upon the characteristics of the equipment used in the gas flow apparatus 44), it is assumed the attached applicator is a GI probe. The GI reference margin distinguishes the back pressure of a GI probe from an endoscopic probe, which is less restrictive. With the desired flow rate set greater than 2 slpm for a GI probe, the flow is automatically reduced to 2 slpm or 1.5 slpm with each activation of the ESU. Care must be taken, however, not to damage the electrode with high electrical power if the power setting is too high. When the activation request is terminated, then the flow rate is returned to the original setting, but no gas flows since the ESU is deactivated.

Table 1 shows an example of the action to be taken for typical ranges of flow rates. The flow rate will be reduced as shown in the action column if the PMEA signal exceeds the specified limits. The established reference voltage (Ref) is typically in the range of 2V to 2.6V. For each range of the displayed flow rate set by the microcontroller 150 (DIAL), a maximum PMEA signal is shown, above which either an occlusion alarm action or gas flow reduction action will occur. For a flow reduction action, the gas flow rate is reduced in appropriate steps, such as 0.5 slpm. In a preferred embodiment, the gas flow rate is reduced only one such step for the current RF activation. For an occlusion alarm action, not only is the gas flow rate inhibited but the electrical energy is terminated and the ESU is deactivated.

In this example, for a desired flow rate in a low range, such as less than about 1.0 slpm, if the PMEA signal is more than the established reference voltage plus an appropriate fold-back margin, such as about 0.3 V, then a flow reduction action is performed wherein the displayed flow rate is reduced by an appropriate amount, such as about 0.5 slpm, as long as the resulting flow rate is not less than an appropriate minimum, such as about 0.1 slpm. If, however, the PMEA signal is more than the established reference voltage plus an appropriate occlusion margin, such as about 0.5 V, then an occlusion alarm action is performed. For a desired flow rate in a medium range, such as between about 1.0 and about 1.5 slpm, if the PMEA signal is more than the established reference voltage plus an appropriate fold-back margin, such as about 0.6 V, then a flow reduction action is performed; but if the PMEA signal is more than the established reference voltage plus an appropriate occlusion margin, such as about 1.2 V, then an occlusion alarm action is performed. For a desired flow rate in an appropriate high range, such as above about 1.5 slpm, if the PMEA signal is more than the established reference voltage plus an appropriate fold-back margin, such as about 0.7 V, then a flow reduction action is performed; but if the PMEA signal is more than the established reference voltage plus an appropriate occlusion margin, such as about 1.3 V, then an occlusion alarm action is performed.

Figure 4A:
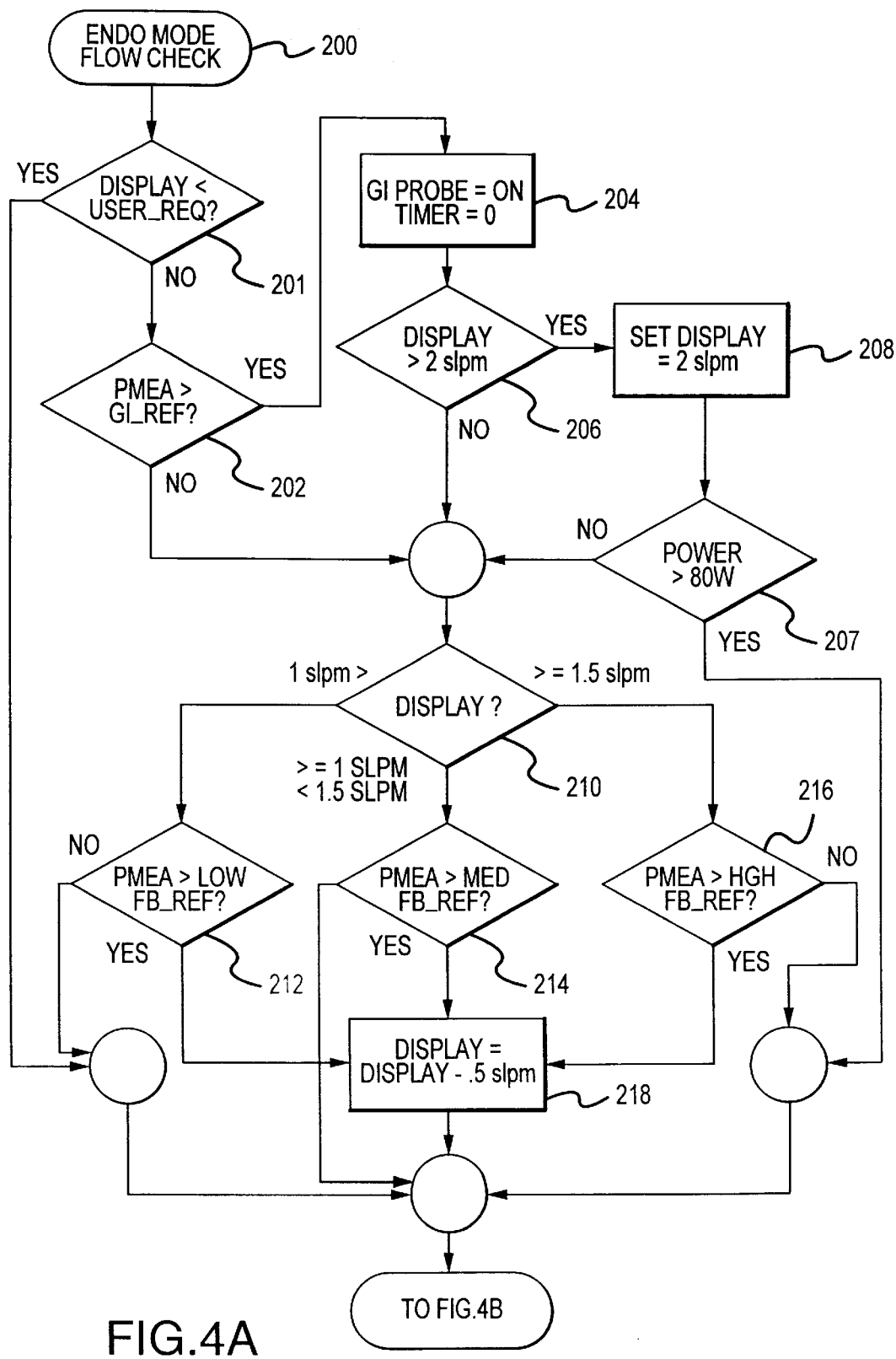
FIGS. 4A, 4B and 4C constitute a single flow chart of the functions performed by the gas delivery apparatus shown in FIG. 2 during an endoscopic mode operating condition, in accordance with the present invention.
Figure 4B:
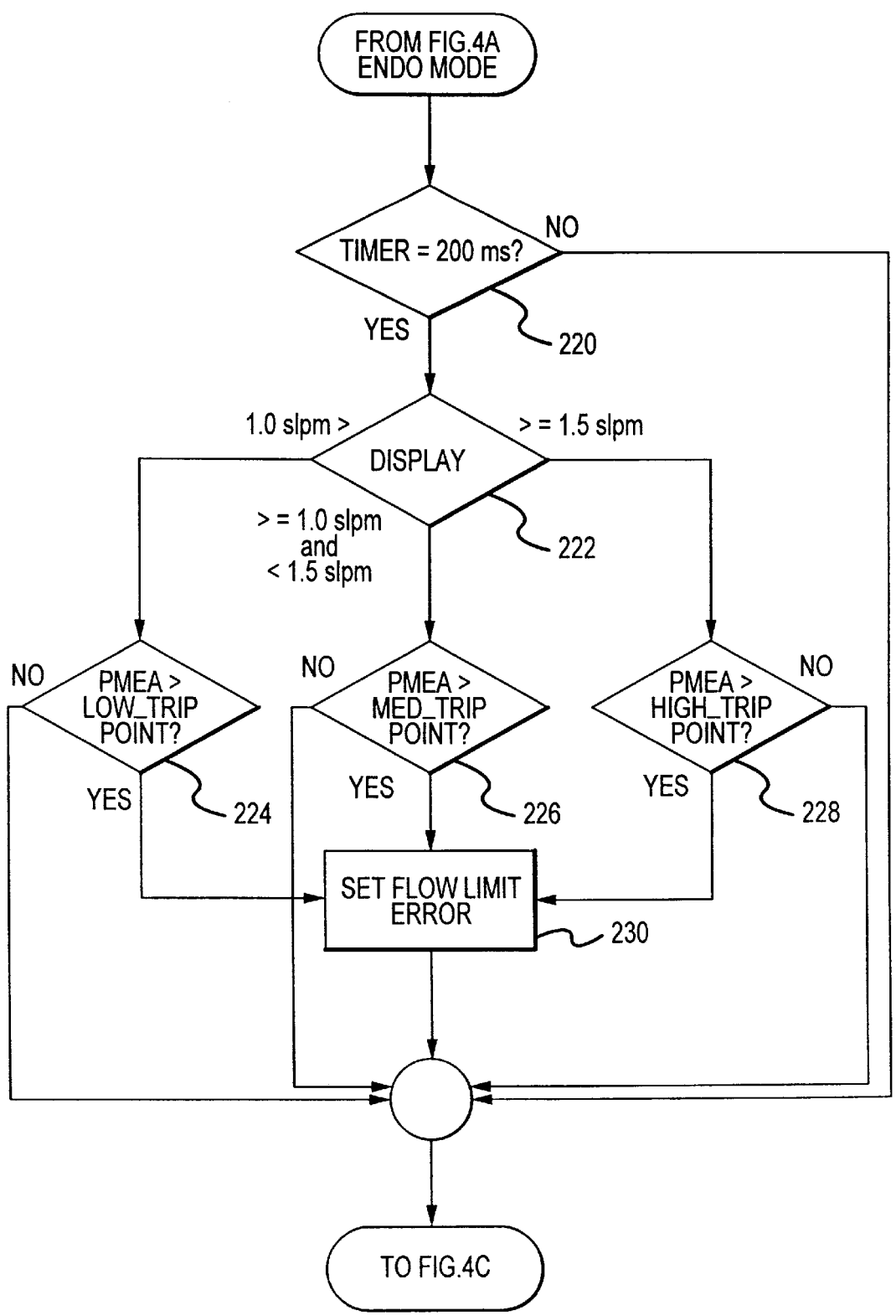
Figure 4C:
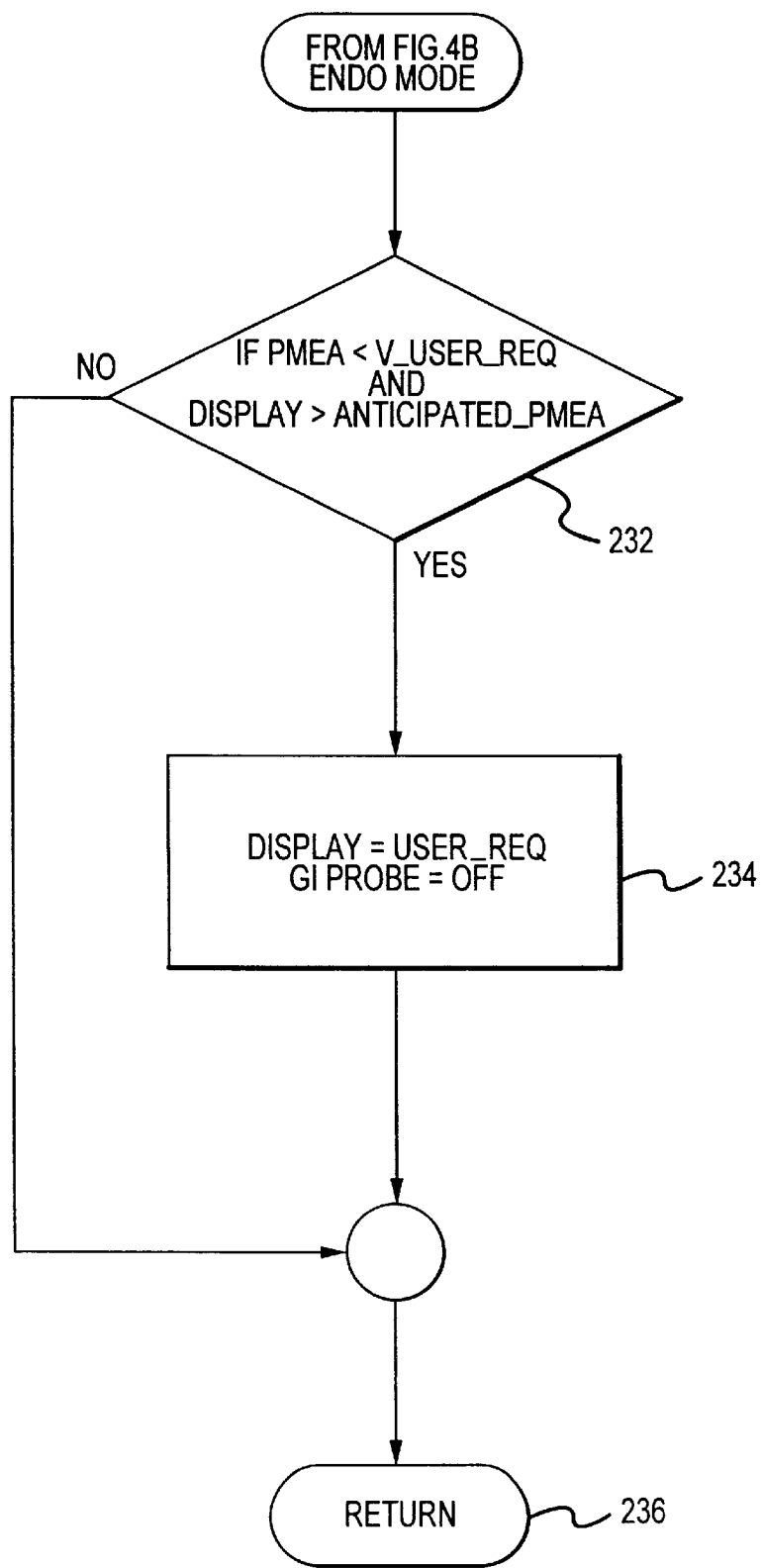

FIGS. 4A, 4B and 4C constitute a flow chart for an exemplary gas flow adjustment procedure in the endo mode. This flow check procedure is executed at appropriate intervals, such as approximately every 100 msec. The microcontroller 150 (FIG. 2) enters the procedure at step 200 and proceeds to step 201 wherein it determines if the displayed flow rate is less than the user-requested setting. This step 201 prevents the procedure from performing the following flow reduction steps more than once, so if the answer is yes at step 201, the procedure branches to step 220 shown in FIG. 4B. If the answer is no at step 201, then it is determined whether the PMEA signal exceeds the permitted GI reference margin (GI$_{13}$ REF) in step 202. If not, then the procedure branches to step 210. But if so, then at step 204, a GI probe indicator flag (GI PROBE) is turned on, to indicate that the procedure assumes the presence of a GI probe; and a timer is initialized to zero, so the occlusion detection procedure can be done after an appropriate time interval. Then in step 206, the procedure determines whether the displayed flow rate is set greater than a maximum value, such as about 2.0 slpm, above which it would be inappropriate to operate a GI probe. If so, then at step 208, the displayed flow rate is reset to the maximum allowable gas flow rate for a GI probe (such as about 2 slpm). Next it is determined in step 207 whether the user-selected power is greater than a predetermined maximum (such as about 80 W), above which the applicator electrode would be damaged if the gas flow rate is set too low. If so, then the control flow branches to step 220 shown in FIG. 4B. In a preferred embodiment, the endo mode will only reduce the gas flow rate once and then hold the flow rate at that value until the conditions are appropriate to return the flow rate to the original user-requested setting (see step 232, FIG. 4C). If the determination at step 206 or 207 is no, the control flow proceeds directly to step 210 without changing the actual flow rate at step 208.

Starting at step 210, the steps are performed to reduce the gas flow rate if the back pressure is too high, but not high enough to shut off the ESU. In step 210, the range of the displayed flow rate is determined. If the displayed flow rate is in an appropriate low range, such as less than about 1.0 slpm, then the procedure determines in step 212 whether the PMEA signal is greater than a low fold back reference voltage (LOW FB_REF), which is the established reference voltage plus an appropriate low fold back margin, such as about 0.3 V. If the displayed flow rate is in a medium range, such as greater than or equal to about 1.0 slpm and less than about 1.5 slpm, then the procedure determines in step 214 whether the PMEA signal is greater than a medium fold back reference voltage (MED FB_REF), which is the established reference voltage plus an appropriate medium fold back margin, such as about 0.6 V. If the displayed flow rate is in a high range, such as greater than or equal to about 1.5 slpm, then the procedure determines in step 216 whether the PMEA signal is greater than a high fold back reference voltage (HIGH FB_REF), which is the established reference voltage plus an appropriate high fold back margin, such as about 0.7 V. If the checked condition in steps 212, 214 or 216 is determined to be true, then this condition indicates too great of a back pressure, so the displayed flow rate provided by the microcontroller 150 to control the proportioning valve 116 is reduced by an appropriate amount, such as about 0.5 slpm (step 218), and control proceeds to step 220 shown in FIG. 4B. If the checked condition in steps 212, 214 or 216 is determined not to be true, then the back pressure is acceptable, so no adjustment is made to the actual flow setting, and control proceeds directly to step 220 shown in FIG. 4B.

Starting in step 220 shown in FIG. 4B, the procedure performs the steps to shut off the ESU 40 when the back pressure is so high that a high risk condition, such as an occlusion, has occurred. In step 220, the procedure determines whether an appropriate time interval (TIMER) has lapsed, such as about 200 msec, so that a complete shut off of the ESU 40 does not happen too quickly, thereby providing time for a transient occlusion problem to be corrected before shut-down. If so, then it is appropriate to reset the timer. If not, the occlusion may be transitory and the procedure branches to the end of the occlusion detection portion of the procedure shown in FIG. 4B. If the appropriate time interval set at step 220 has lapsed, then the procedure determines the range of the displayed flow rate in step 222. If the displayed flow rate is in a low range, such as less than about 1.0 slpm, then the procedure determines in step 224 whether the PMEA signal is greater than a low alarm trip reference voltage (LOW_TRIP POINT), which is the established reference voltage plus an appropriate low occlusion margin, such as about 0.5 V. If the displayed flow rate is in a medium range, such as greater than or equal to about 1.0 slpm and less than about 1.5 slpm, then the procedure determines in step 226 whether the PMEA signal is greater than a medium alarm trip reference voltage (MED_TRIP POINT), which is the established reference voltage plus an appropriate medium occlusion margin, such as about 1.2 V. If the displayed flow rate is in a high range, such as greater than or equal to about 1.5 slpm, then the procedure determines in step 228 whether the PMEA signal is greater than a high alarm trip reference voltage (HIGH_ TRIP POINT), which is the established reference voltage plus an appropriate high occlusion margin, such as about 1.3 V. The alarm trip reference voltages are the cutoff point above which an occlusion alarm needs to be set, so if the checked condition in steps 224, 226 or 228 is determined to be true, then this condition indicates that the back pressure is so high that an occlusion may be interfering with the safe performance of the ESU 40, so the procedure deactivates the ESU 40 and sets a flow limit error (step 230), indicating an occlusion alarm condition, and provides alarm and display indications to the user at the displays 76 and alarm 78 (FIG. 1). Thereafter the control flow proceeds to step 232 shown in FIG. 4C. If the checked condition in steps 224, 226 or 228 is determined not to be true, then it is assumed that there is no occlusion condition, so control proceeds directly to step 232 shown in FIG. 4C.

In step 232 shown in FIG. 4C, the procedure determines whether it is appropriate to return the displayed flow rate to the original user-requested setting. In step 232, it is determined if the PMEA signal is less than a V_USER_REQ signal, which is the established reference voltage plus the anticipated incremental increase that would result from the user-requested setting minus an appropriate margin, such as about 19 mV, an experimentally established safe value. Also determined in step 232 is whether the displayed flow rate is greater than the current anticipated flow rate equivalent of the PMEA signal. If the answer in step 232 is yes, the displayed flow rate is set to the user-requested setting and the GI Probe signal is turned off (step 234) and the procedure ends (step 236). Otherwise, as determined at step 232, the procedure ends without returning the settings to their original values.

It is understood that the maximum limits for the measured back pressure (PMEA) shown in FIGS. 4A, 4B and 4C are exemplary only and that experience or experimentation may indicate that different limits would be more appropriate in different applications. Additionally, different responses to different back pressure conditions may be found to be appropriate for different applications.

The automatic mode of operation for the ESU is selected primarily for open surgical procedures, where gas flow rates of up to 10 slpm are commonly used. The automatic mode, referred to herein as the "auto" mode, operates on essentially the same principle as the endo mode to reduce or completely inhibit the flow of gas or operation of the ESU 40. In the auto mode, the gas flow rate is adjusted relative to the power setting of the ESU 40, although it is understood that the auto mode may include any situation in which the surgeon does not manually control the flow rate, but merely sets a desired power level and allows the ESU 40 to automatically adjust the flow rate as appropriate.

In the auto mode, it is preferred that the gas flow be reduced, or be "folded back," in single liter increments, to attempt to keep the measured back pressure within defined and appropriate limits. Different sized steps or even a continuous adjustment in gas flow may be used in other embodiments or other applications. It is also preferred that the rate of flow be reduced to no less than 4 slpm or some other appropriate minimum value. Thus, if the desired flow setting is at 10 slpm, then the flow can be reduced only by as much as 6 slpm. If the minimum flow rate is reached and the maximum pressure limit occurs, then an alarm will be set and the ESU will be deactivated.

For each user-requested setting, the limit at which the flow rate will be folded back preferably occurs at essentially the same point, such as when the PMEA signal exceeds the established reference voltage plus an anticipated incremental increase indicated by the user-requested setting plus an experimentally determined appropriate fold back margin. Such an appropriate margin may be about three analog-to-digital (A/D) conversion counts of the microcontroller 150 (FIG. 2), which is three times the A/D resolution. An occlusion alarm will result when the PMEA signal exceeds an absolute maximum at any flow rate, such as about 3.3 V, or when the PMEA signal exceeds the established reference voltage plus the anticipated incremental increase due to the user-requested setting plus an appropriate occlusion margin, such as about ten A/D counts. It is preferred that the occlusion alarm effectively shut down the ESU 40 by inhibiting the RF energy transferred and the gas flow. The occlusion alarm condition may have to be maintained for an appropriate length of time before the alarm actually results.

For example, the resolution of the analog-to-digital converter (not shown) of the control microcontroller 150 (FIG. 2) may be about 0.02 V per A/D count, or bit. For this example, Table 2 illustrates typical anticipated and fold back limits for each user-requested setting from 4 to 10 slpm. This example assumes that the displayed flow rate has a lower limit of 4 slpm. The fold back voltage is 3 counts, or about 0.06 V, above the Ref plus anticipated voltage for each user-requested setting. After the displayed flow rate has been folded back, the procedure will check to see if the PMEA signal exceeds the new fold back limit. It is also preferred that, after a fold back, the PMEA signal be compared to the fold back limit at the original user-requested setting. In other words, in this example, if the original user-requested setting was 10 slpm, then after each fold back occurrence, the next check of the PMEA signal will compare the actual PMEA signal to 2.45 V, the fold back limit for a user-requested setting of 10 slpm. The maximum voltage for PMEA at which an occlusion alarm will be set is shown as about 10 counts, or about 0.2 V, above the Ref plus anticipated voltage for each user-requested setting.

TABLE 2

| DIAL (slpm) | PMEA (anticipated) | PMEA (foldback) | PMEA (occlusion) |
|---|---|---|---|
| 10 | 2.39 V | 2.45 V | 2.59 V |
| 9 | 2.35 V | 2.41 V | 2.55 V |
| 8 | 2.31 V | 2.37 V | 2.51 V |
| 7 | 2.27 V | 2.33 V | 2.47 V |
| 6 | 2.24 V | 2.30 V | 2.44 V |
| 5 | 2.20 V | 2.26 V | 2.40 V |
| 4 | — | — | — |

Figure 5:
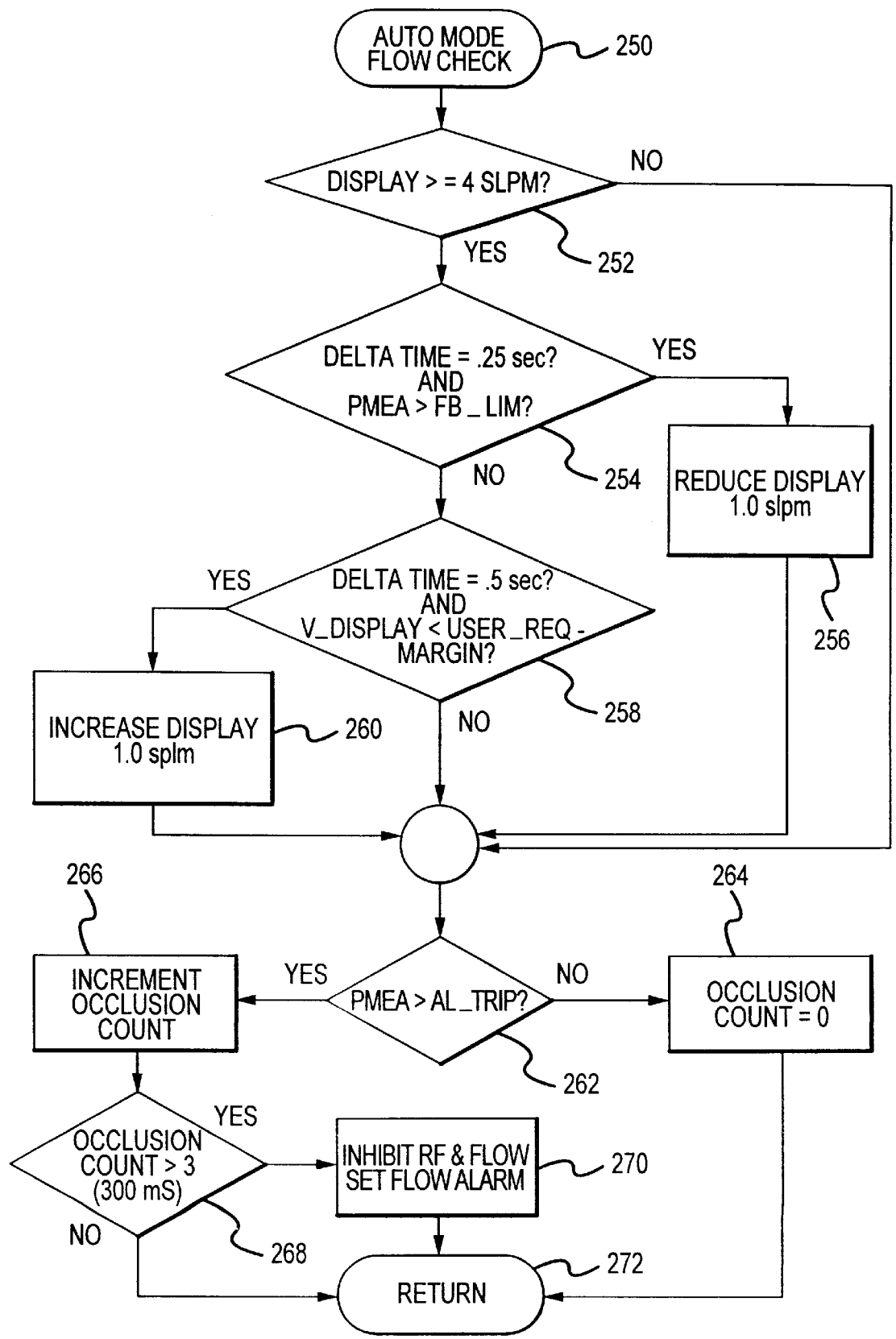
FIG. 5 is a flow chart of the functions performed by the gas delivery apparatus shown in FIG. 2 during an automatic mode operating condition, in accordance with the present invention.

The auto mode flow check procedure is illustrated by the flow chart shown in FIG. 5. This flow check procedure is executed at appropriate intervals, such as approximately every 100 msec. The microcontroller 150 enters the procedure at step 250 and proceeds to determine whether the displayed flow rate is greater than a predetermined minimum value, such as about 4 slpm in this example (step 252). In this example, the minimum flow rate for an auto mode procedure is assumed to be 4 slpm. If the answer at step 252 is no, then control branches to step 262 where the check to determine if an occlusion condition exists begins. Otherwise, the procedure checks whether the displayed flow rate needs to be reduced (step 254) by determining whether the PMEA signal is greater than an appropriate fold back limit (FB_LIM), which is the established reference (Ref) voltage plus the anticipated incremental increase over the Ref voltage indicated by the user-requested setting plus an appropriate offset. In this example, the offset is about 59 mV, or three counts of the analog-to-digital converter that delivers the PMEA signal to the microcontroller 150. The procedure also checks to make sure that an appropriate time interval (DELTA TIME) has passed since the last flow check was done so that a sufficient amount of time will have elapsed to allow any previous flow changes to stabilize in the gas flow path. In this example, the time interval is shown as 0.25 seconds, but may be any appropriate value. The clock that counts this time interval is reset each time the flow rate is changed. If the answer is yes in step 254, then the procedure reduces the displayed flow rate by a predetermined appropriate amount, such as about 1 slpm (step 256). As indicated, this step will not be permitted to reduce the gas flow rate below the stated minimum, about 4 slpm in this example. If, however, the answer is no in step 254, then the procedure checks (step 258) whether conditions are right for the gas flow rate to be increased to return the gas flow rate closer to its original value.

The fold back can occur with certain applicators, particularly those with a non-standard nozzle, a smaller nozzle, or an applicator which has restricted flow because of its length. These types of applicators will cause the flow to fold back from the original user-requested setting. The number of increments that the flow rate is reduced will usually depend on the initial user-requested setting. For example, the flow may be reduced by only one interval, or about 1 slpm, at a relatively low initial user-requested setting, but the flow rate may be reduced by a larger amount, such as about 4 slpm (four 1-slpm intervals), at a relatively high initial user-requested setting. In other cases, an applicator may be used at initial moderate or low flow rates, but a higher flow rate may cause flow or occlusion alarms, in which case the manual mode of operation should be selected for use.

At step 258, the flow procedure again makes sure that an appropriate time interval (DELTA TIME), such as about 0.5 sec in this example, has elapsed. For example, the procedure will take about one and a half seconds to return the flow rate to the original setting in a case where the gas flow rate has been reduced by three intervals, or about 3 slpm in this example. Also, the voltage equivalent of the displayed flow rate must be less than the established reference voltage plus the anticipated incremental increase due to the user-requested setting minus an appropriate margin, such as about 39 mV (or two counts of the A/D converter). If the answer is yes at step 258, then the back pressure conditions are acceptable for the displayed flow rate to be increased one interval back toward the user-requested setting, so the procedure in this example increases the displayed flow rate by 1 slpm at step 260 and proceeds to step 262. Otherwise, the procedure continues directly to step 262 to begin the check for an occlusion condition.

At step 262, the procedure determines whether the PMEA signal is greater than an occlusion alarm trip limit (AL_TRIP), which is the established reference voltage plus the anticipated incremental increase due to the user-requested setting plus an appropriate occlusion margin, above which an occlusion would be expected to have occurred. In this example, the margin is shown as about 0.2 V, or ten counts of the A/D converter. If the answer is yes, then the procedure increments a counter (occlusion count) at step 266 and then checks whether the occlusion count is greater than 3 (step 268). In this manner, since this exemplary flow check procedure is performed about once every 100 msec, the occlusion condition that triggered the yes answer in step 262 will have to exist for about 300 msec before an occlusion alarm will actually be set. This delay prevents the ESU 40 from deactivating too quickly due to an occlusion and provides time for the occlusion to be cleared. Once the occlusion count goes over 3, the procedure deactivates the ESU 40 by inhibiting the RF signal and the gas flow and displays a flow alarm (step 270). If the conditions do not indicate a possible occlusion in step 262, then the procedure resets the occlusion count to zero (step 264). The procedure ends in step 272.

It is understood that other applications of the gas flow regulation technique and apparatus shown herein may preferably require different parameters to be checked to determine whether the gas flow rate needs to be reduced or increased or if the ESU apparatus needs to be deactivated. The parameters shown in the above example are shown for illustrative purposes only and are not intended to restrict the scope of the invention.

In the manual mode of operation of the ESU, the user or surgeon controls the actual flow rate directly, so the gas flow rates will not automatically reduce in the event of a too high back pressure condition, as is the case in the auto mode. Rather, the manual mode will only detect an occlusion, set an alarm and deactivate the ESU 40 to prevent potentially serious conditions. Table 3 illustrates an example of the manual mode in which an alarm is set when the PMEA signal exceeds the PMEA maximum limit shown for a particular user-requested setting. The typical line pressure at the maximum limit in the gas flow path is also shown. It is also preferred that the manual mode have an appropriate maximum PMEA signal limit (such as about 3.3 V) that applies regardless of the requested flow setting.

TABLE 3

| REQUESTED FLOW RATE (slpm) | PMEA MAXIMUM | LINE PRESSURE (mmHg/psi) |
| --- | --- | --- |
| 10 | 3.17 V | 344/6.6 |
| 9 | 3.13 V | 332/6.4 |
| 8 | 3.09 V | 321/6.2 |
| 7 | 3.05 V | 309/6.0 |
| 6 | 3.02 V | 298/5.8 |
| 5 | 2.97 V | 286/5.5 |
| 4 | 2.94 V | 275/5.3 |

FIG. 6 illustrates an example of the manual mode flow check procedure. Preferably, this procedure is performed at appropriate intervals, such as about every 100 msec. The control microcontroller 150 enters the procedure at step 300 and proceeds to check in step 302 if the PMEA signal is greater than the allowable maximum limit, which includes two conditions for a possible occlusion condition: whether the PMEA signal is greater than the permissible maximum limit (about 3.3 V in this example) for all requested flow settings, and whether the PMEA signal is greater than the established reference voltage plus the anticipated incremental increase due to the displayed flow rate plus an appropriate occlusion margin (about 0.78 V in this example). If either condition is true, then the procedure deactivates the ESU 40 by inhibiting the RF signal and the gas flow and displays a flow alarm (step 304) before branching to the end (step 312). If the answer is no in step 302, then in a preferred embodiment, the procedure checks in step 306 to determine if the soft start procedure (FIG. 3) is still in effect. If so, then it is preferred to make sure that no occlusion exists at this point before permitting soft start to increase the displayed flow rate to the user-requested setting. This check gives the surgeon more opportunity to correct the occlusion condition before a higher gas flow rate is provided. Thus, in step 308, it is determined if the PMEA signal is greater than an appropriate test limit, such as the established reference voltage plus the anticipated incremental increase due to the displayed flow rate plus an appropriate margin, such as about three counts of the A/D converter. If the answer in step 308 is yes, the displayed flow rate is set to 2 slpm in step 310, such that the soft start procedure cannot reset the displayed flow rate to a higher value. If either answer to steps 306 or 308 is no, then the procedure ends in step 312.

It is understood that other operational parameters may be determined to be preferable in different applications of the gas flow adjustment technique and apparatus described herein for a manual mode of operation of an ESU 40. It is further understood that other modes of operation besides the endo, auto and manual modes described herein may be defined for use with the gas flow adjustment technique and apparatus described herein. Thus, the examples provided above are intended to be illustrative only and not intended to limit the scope of the invention.

The exemplary operational modes described above illustrate advantages of the gas flow adjustment apparatus and method especially with respect to safety during a surgical procedure. The gas flow reduction steps in the endo and auto modes significantly reduce the risk of embolism during a surgical procedure. Additionally, the reduced flow rates provide an opportunity to clear up transitory occlusion conditions before a sudden over-pressurization occurs or before the ESU is de-activated, so the improvements not only help to compensate for the skills of the surgeon, but also help to maintain a convenient working condition for the surgeon without unwanted annoyances due to equipment de-activations. The back pressure-detection features permit operations with many different applicators having unusual flow path diameters and lengths or curvatures. The reduced flow rates also help to maintain a consistent and proper arc transfer for uniform creation of eschar in the tissue. Many other advantages and improvements will be apparent to those having skill in the art, after gaining a complete understanding and comprehension of the present invention.

Presently preferred embodiments of the invention and its improvements have been described with a degree of particularity. This description has been made by way of preferred example. It should be understood that the scope of the present invention is defined by the following claims, and should not be unnecessarily limited by the detailed description of the preferred embodiment set forth above.

The invention claimed is:

1. A gas delivery apparatus for gas-assisted electrocoagulation in which a flow of gas is supplied in a flowpath to an applicator and the gas is ionized at the applicator to transfer electrical energy in arcs to coagulate bleeding from tissue in response to an electrocoagulation activation request, comprising:
   a gas flow-controlling valve connected in the flowpath; and
   a flow controller connected to the valve and responsive to the activation request to supply a control signal to the valve to set an initiation gas flow rate in the flowpath to more readily initiate the transfer of arcs from the applicator, the controller also supplying a control signal to the valve to set an electrocoagulation gas flow rate in the flowpath to conduct the arcs during electrocoagulation after initiation of the arc transfer, the initiation gas flow rate being less than the electrocoagulation gas flow rate.

2. A gas delivery apparatus as defined in claim 1 wherein the initiation gas flow rate occurs for a predetermined time duration after the occurrence of the activation request.

3. A gas delivery apparatus as defined in claim 1 wherein the initiation gas flow rate is set only if the electrocoagulation gas flow rate exceeds a predetermined value.

4. A gas delivery apparatus as defined in claim 1, further comprising:
   a pressure sensor connected in the flowpath and connected to the controller to supply a signal related to pressure in the flowpath resulting from the gas flow in the flowpath; and wherein:
   the controller controls the valve to terminate the gas flow in the flowpath upon the pressure-related signal exceeding a predetermined pressure limit.

5. A gas delivery apparatus as defined in claim 4 wherein:
   the controller controls the valve to set the initiation gas flow rate for a predetermined time after the occurrence of the activation request; and
   the controller controls the valve to terminate the gas flow upon the pressure-related signal exceeding the predetermined pressure limit during the predetermined time of the initiation gas flow rate.

6. A gas delivery apparatus as defined in claim 5 wherein:
   the pressure limit first aforesaid applies during initiation gas flow rates;
   the controller also controls the valve to terminate the gas flow upon the pressure-related signal exceeding a second predetermined pressure limit which is different from the first predetermined pressure limit, the second predetermined pressure limit applying during electrocoagulation gas flow rate conditions; and
   the controller controls the valve to terminate the gas flow upon the pressure-related signal exceeding the second predetermined pressure limit after the cessation of the initiation gas flow rate and during the electrocoagulation gas flow rate.

7. A gas delivery apparatus as defined in claim 5 wherein:
   the controller also terminates the gas flow upon the pressure-related signal exceeding a second predetermined pressure limit which is different from that predetermined limit first aforesaid, the second predetermined pressure limit applying after expiration of the predetermined time during which the initiation gas flow rate occurs.

8. A gas delivery apparatus as defined in claim 1 further comprising:
   a pressure sensor connected in the flowpath and connected to the controller to supply a signal related to pressure in the flowpath resulting from the gas flow in the flowpath; and wherein:
   the controller responds to the pressure-related signal to determine whether an occlusion condition is present in the flowpath.

9. A gas delivery apparatus as defined in claim 8 wherein:
   the controller controls the valve to reduce the gas flow rate in the flowpath by a predetermined increment in response to the pressure-related signal indicating a partial occlusion condition in the flowpath.

10. A gas delivery apparatus as defined in claim 9 wherein:
    the controller controls the valve to increase the gas flow rate in the flowpath in response to the pressure-related signal indicating a dissipation of the partial occlusion in the flowpath.

11. A gas delivery apparatus as defined in claim 1 further comprising:
    a pressure sensor connected in the flowpath and connected to the controller to supply a signal related to pressure in the flowpath resulting from the gas flow in the flowpath; and wherein:
    the controller controls the valve to terminate the gas flow in the flowpath upon the pressure-related signal exceeding a predetermined alarm limit.

12. A gas delivery apparatus as defined in claim 1 further comprising:
    a pressure sensor connected in the flowpath and connected to the flow controller to supply a signal related to pressure in the flowpath resulting from the gas flow in the flowpath; and wherein:
    the controller determines the type of applicator connected in the flowpath in response to the pressure-related signal.

13. A gas delivery apparatus as defined in claim 12 wherein:
    the controller controls the valve to establish a maximum gas flow rate through the flowpath to the determined type of applicator in response to the pressure-related signal.

14. A gas delivery apparatus as defined in claim 1 further comprising:
    a selector to establish a user requested electrocoagulation gas flow rate and to supply a signal to the controller related to the user requested electrocoagulation gas flow rate;

a sensor connected in the flowpath to measure a mass flow rate of gas in the flowpath and to supply a signal to the controller related to the mass flow rate; and wherein:

the controller controls the valve in relation to a difference between the user requested gas flow rate signal and the mass flow rate-related signal.

15. A gas delivery apparatus for gas-assisted electrocoagulation in which a flow of gas is supplied in a flowpath to an applicator in response to an electrocoagulation activation request and the gas is ionized at the applicator to transfer electrical energy in arcs to coagulate bleeding from tissue, comprising:

a gas flow-controlling valve connected in the flowpath;

a selector to establish a user requested electrocoagulation gas flow rate in the flowpath and to supply a signal related to the user requested electrocoagulation gas flow rate;

a pressure sensor connected in the flowpath and operative to supply a signal related to pressure in the flowpath resulting from the gas flow in the flowpath; and a flow controller connected to the valve and receptive of the pressure-related signal and the user requested flow rate signal, the controller controlling the valve to reduce the gas flow rate in the flowpath from the electrocoagulation gas flow rate corresponding to the user requested flow rate upon the pressure-related signal indicating a pressure in the flowpath exceeding a predetermined limit.

16. A gas delivery apparatus as defined in claim 15 wherein:

the controller determines the type of applicator connected in the flowpath in response to the pressure-related signal.

17. A gas delivery apparatus as defined in claim 15 wherein:

the controller establishes a maximum gas flow rate to the applicator in response to the relationship of the pressure-related signal to one of either a predetermined maximum pressure limit or the user requested flow rate signal.

18. A gas delivery apparatus as defined in claim 17 wherein:

the controller controls the valve to terminate the flow of gas in the flowpath in response to the pressure-related signal exceeding the predetermined maximum pressure limit.

19. A gas delivery apparatus as defined in claim 18 in combination with an electrosurgical generator connected to deliver electrical energy to the applicator for ionizing the gas and transferring electrical energy in arcs, and wherein:

the controller is connected to the generator to control the generator to terminate the delivery of electrical energy in response to the termination of gas flow in the flowpath.

20. A gas delivery apparatus as defined in claim 18 in combination with an electrosurgical generator connected to deliver electrical energy to the applicator for ionizing the gas and transferring electrical energy in arcs, and wherein:

the controller is connected to the generator to control the generator to terminate the delivery or electrical energy in response to the pressure-related signal exceeding the predetermined maximum pressure limit.

21. A gas delivery apparatus as defined in claim 15 wherein:

the controller controls the valve to increase the gas flow rate in the flowpath to the gas flow rate corresponding to the user requested flow rate signal upon the pressure-related signal indicating that the pressure in the flowpath has decreased below the predetermined pressure limit.

22. A gas delivery apparatus as defined in claim 21 in combination with an electrosurgical generator connected to deliver electrical energy to the applicator for ionizing the gas and transferring electrical energy in arcs, and wherein:

the user requested flow rate signal is established in relation to a user requested power level for the electrosurgical generator.

23. A gas delivery apparatus as defined in claim 15 wherein:

the controller determines whether one of a gastrointestinal probe applicator or an endoscopic probe applicator is connected in the flowpath in response to the pressure-related signal; and the controller controls the valve to establish predetermined maximum flow rates for the gastrointestinal probe applicator and for the endoscopic probe applicator, and the predetermined maximum flow rate for the gastrointestinal probe is less than the predetermined maximum flow rate for the endoscopic probe applicator.

24. A gas delivery apparatus as defined in claim 23 wherein:

the controller controls the valve to establish the maximum gas flow rate in the flowpath to the gastrointestinal probe applicator on the basis of the smaller one of the predetermined maximum flow rate for the gastrointestinal probe applicator or the gas flow rate corresponding to the user requested flow rate signal.

25. A gas delivery apparatus as defined in claim 24 wherein:

the controller controls the valve to reduce the gas flow rate in the flowpath to the gastrointestinal probe applicator by an incremental amount in response to the pressure-related signal exceeding a predetermined fold pressure limit which is related to gas flow rate in the flowpath immediately before the reduction in gas flow rate.

26. A gas delivery apparatus as defined in claim 25 wherein:

the controller controls the valve to terminate the flow of gas in the flowpath in response to the pressure-related signal exceeding a predetermined trip point pressure limit related to the gas flow rate in the flowpath immediately before the termination of the gas flow.

27. A gas delivery apparatus as defined in claim 25 wherein:

the controller controls the valve to increase the gas flow rate in the flowpath to the gastrointestinal probe applicator by an incremental amount in response to the pressure-related signal falling below an increase-inducing predetermined pressure limit related to the predetermined fold pressure limit.

28. A gas delivery apparatus as defined in claim 23 wherein:

the controller controls the valve to establish the maximum gas flow rate in the flowpath to the endoscopic probe applicator on the basis of the smaller one of the predetermined maximum flow rate for the endoscopic probe applicator or the gas flow rate corresponding to the user requested flow rate signal.

29. A gas delivery apparatus as defined in claim 28 wherein:

the controller controls the valve to terminate the flow of gas in the flowpath in response to the pressure-related signal exceeding a predetermined trip point pressure limit related to the gas flow rate in the flowpath immediately before the termination of the gas flow.

30. A gas delivery apparatus as defined in claim 28 wherein:
   the controller controls the valve to increase the gas flow rate in the flowpath by an incremental amount to the endoscopic probe applicator in response to the pressure-related signal falling below an increase-inducing predetermined pressure limit related to a predetermined maximum pressure limit for the endoscopic probe applicator.

31. A gas delivery apparatus as defined in claim 15 in combination with an electrosurgical generator connected to deliver electrical energy to the applicator for ionizing the gas and transferring electrical energy in arcs, and wherein:
   the user requested flow rate signal is established in relation to a user requested power level for the electrosurgical generator.

32. A gas delivery apparatus as defined in claim 31, wherein the applicator is an open surgery applicator.

33. A gas delivery apparatus as defined in claim 15 further comprising:
   a gas flow sensor connected in the flowpath to supply a gas flow rate signal related to the amount of gas flowing in the flowpath; and wherein:
   the controller receives the gas flow rate signal and determines an actual gas flow rate in the flowpath;
   the controller further determines whether the gas flow rate is within one of a plurality of predetermined different gas flow ranges;
   the controller controls the valve to reduce the gas flow rate in the flowpath upon the pressure-related signal indicating a pressure in the flowpath which exceeds a predetermined limit for a predetermined gas flow range.

34. A method of gas-assisted electrocoagulation in which a flow of gas is supplied in a flowpath to an applicator and the gas is ionized at the applicator to transfer electrical energy in arcs to coagulate bleeding from tissue, comprising the steps of:
   flowing gas in the flowpath to the applicator;
   initially setting an initiation gas flow rate to the applicator;
   transferring electrical energy in arcs to the tissue in the gas flowing from the applicator at the initiation gas flow rate; and
   setting the gas flow rate to an electrocoagulation gas flow rate after the arcs have been transferred to the tissue and while continuing to transfer arcs in the gas flowing at the electrocoagulation gas flow rate, the electrocoagulation gas flow rate being greater than the initiation gas flow rate.

35. A method as defined in claim 34 further comprising the steps of:
   maintaining the initiation gas flow rate for a predetermined time period after commencing the delivery of the initiation gas flow rate.

36. A method as defined in claim 34 further comprising the steps of:
   sensing pressure in the flowpath; and
   reducing the initiation gas flow rate in the flowpath upon the sensed pressure in the flowpath exceeding a predetermined initiation pressure limit while the gas flows at the initiation gas flow rate.

37. A method as defined in claim 36 further comprising the step of:
   terminating the initiation gas flow rate in the flowpath upon the sensed pressure in the flowpath exceeding a second predetermined initiation pressure limit which is greater than the predetermined initiation pressure limit first aforesaid while the gas flows at the initiation gas flow rate.

38. A method as defined in claim 37 further comprising the step of:
   reducing the electrocoagulation gas flow rate in the flowpath upon the sensed pressure in the flowpath exceeding a predetermined electrocoagulation pressure limit while the gas flows at the electrocoagulation gas flow rate.

39. A method as defined in claim 38 further comprising the step of:
   terminating the electrocoagulation gas flow rate in the flowpath upon the sensed pressure in the flowpath exceeding a second predetermined electrocoagulation pressure limit which is greater than the predetermined electrocoagulation pressure limit first aforesaid while the gas flows at the initiation gas flow rate.

40. A method as defined in claim 34 further comprising the steps of:
   sensing pressure in the flowpath; and
   reducing the electrocoagulation gas flow rate in the flowpath upon the sensed pressure in the flowpath exceeding a predetermined electrocoagulation pressure limit while the gas flows at the electrocoagulation gas flow rate.

41. A method as defined in claim 40 further comprising the step of:
   terminating the electrocoagulation gas flow rate in the flowpath upon the sensed pressure in the flowpath exceeding a second predetermined electrocoagulation pressure limit which is greater than the predetermined electrocoagulation pressure limit first aforesaid while the gas flows at the initiation gas flow rate.

42. A method as defined in claim 34 further comprising the steps of:
   requesting a value of the electrocoagulation gas flow rate;
   determining whether the requested electrocoagulation gas flow rate exceeds a predetermined value; and
   setting the initiation gas flow rate to the electrocoagulation gas flow rate if the requested electrocoagulation gas flow rate does not exceed the predetermined value.

43. A method as defined in claim 34 wherein the step of sensing pressure in the flowpath further comprises the step of:
   sensing a pressure in the flowpath which relates to a back pressure resulting from the gas flow in the flowpath.

44. A method as defined in claim 43 further comprising the step of:
   determining whether an occlusion condition is present in the flowpath based on the sensed pressure.

45. A method as defined in claim 44 further comprising the step of:
   reducing the gas flow rate in the flowpath in response to the sensed pressure indicating a partial occlusion condition in the flowpath.

46. A method as defined in claim 44 further comprising the step of:
   reducing the gas flow rate in the flowpath by a predetermined increment in response to the sensed pressure indicating a partial occlusion condition in the flowpath.

47. A method as defined in claim 44 further comprising the step of:
increasing the gas flow rate in the flowpath in response to the sensed pressure indicating a dissipation of the partial occlusion condition in the flowpath.

48. A method as defined in claim 44 further comprising the step of:
establishing a maximum gas flow rate for the applicator in response to the sensed pressure.

49. A method as defined in claim 43 further comprising the step of:
determining the type of applicator connected in the flowpath in response to the sensed pressure.

50. A method as defined in claim 49 further comprising the step of:
flowing gas at a maximum gas flow rate through the flowpath to the determined type of applicator in response to the pressure-related signal.

51. A method as defined in claim 34 further comprising the steps of:
requesting a value of the electrocoagulation gas flow rate;
measuring a mass flow rate of gas in the flowpath; and
varying the gas flow through the flowpath relative to any difference between the requested gas flow rate and the measured mass flow rate.

52. A method of gas-assisted electrocoagulation in which a flow of gas is supplied in a flowpath to an applicator and the gas is ionized at the applicator to transfer electrical energy in arcs to coagulate bleeding from tissue, comprising the steps of:
flowing gas through the flowpath;
sensing a pressure in the flowpath resulting from gas flow in the flowpath; and
reducing the gas flow rate in the flowpath without terminating the gas flow in the flowpath upon the sensed pressure exceeding a predetermined limit.

53. A method as defined in claim 52 further comprising the step of:
terminating the flow of gas in the flowpath in response to the sensed pressure exceeding a predetermined maximum pressure limit.

54. A method as defined in claim 53 further comprising the steps of:
delivering electrical energy to the applicator to ionize the gas and transfer electrical energy in arcs; and
terminating the delivery of electrical energy in response to the termination of gas flow in the flowpath.

55. A method as defined in claim 52 further comprising the steps of:
requesting a value of the electrocoagulation gas flow rate; and
establishing a maximum gas flow rate to the applicator in response to the relationship of the sensed pressure to one of either a predetermined maximum pressure or the requested electrocoagulation flow rate.

56. A method as defined in claim 52 comprising the steps of:
requesting a value of the electrocoagulation gas flow rate; and
increasing the gas flow rate in the flowpath to the gas flow rate corresponding to the requested flow rate value upon the sensed pressure decreasing below the predetermined limit.

57. A method as defined in claim 52 further comprising the steps of:
delivering electrical energy at a power level to ionize the gas and transfer electrical energy in arcs; and
setting the electrocoagulation gas flow rate in relation to the power level of the delivered electrical energy.

58. A method of gas-assisted electrocoagulation in which a flow of gas is supplied in a flowpath to an applicator and the gas is ionized at the applicator to transfer electrical energy in arcs to coagulate bleeding from tissue, comprising the steps of:
flowing gas through the flowpath;
sensing a pressure in the flowpath resulting from gas flow in the flowpath;
reducing the gas flow rate in the flowpath upon the sensed pressure exceeding a predetermined limit; and
determining the type of applicator connected in the flowpath from sensing the pressure in the flowpath.

59. A method of gas-assisted electrocoagulation in which a flow of gas is supplied in a flowpath to an applicator and the gas is ionized at the applicator to transfer electrical energy in arcs to coagulate bleeding from tissue, comprising the steps of:
flowing gas through the flowpath;
sensing a pressure in the flowpath resulting from gas flow in the flowpath;
reducing the gas flow rate in the flowpath upon the sensed pressure exceeding a predetermined limit;
determining whether one of a gastrointestinal probe applicator or an endoscopic probe applicator is connected in the flowpath by sensing the pressure; and
establishing predetermined maximum flow rates for the gastrointestinal probe applicator and for the endoscopic probe applicator, the predetermined maximum flow rate for the gastrointestinal probe being less than a predetermined maximum flow rate for the endoscopic probe applicator.

60. A method as defined in claim 59 further comprising the steps of:
requesting a value of the electrocoagulation gas flow rate; and
establishing the maximum gas flow rate in the flowpath to the gastrointestinal probe applicator on the basis of the smaller one of a predetermined maximum flow rate for the gastrointestinal probe applicator or the requested gas flow rate.

61. A method of gas-assisted electrocoagulation in which a flow of gas is supplied in a flowpath to an applicator and the gas is ionized at the applicator to transfer electrical energy in arcs to coagulate bleeding from tissue, comprising the steps of:
flowing gas through the flowpath;
sensing a pressure in the flowpath resulting from gas flow in the flowpath;
reducing the gas flow rate in the flowpath upon the sensed pressure exceeding a predetermined limit;
measuring the gas flow rate in the flowpath;
determining one of a plurality of predetermined different gas flow ranges in which the measured gas flow rate falls; and
reducing the gas flow rate in the flowpath upon the sensed pressure in the flowpath exceeding a predetermined limit for the predetermined gas flow range within which the measured gas flow rate falls.

* * * * *